United States Patent [19]

Illig et al.

[11] Patent Number: 5,326,553

[45] Date of Patent: * Jul. 5, 1994

[54] COMPOSITIONS OF IODOPHENOXY ALKANES AND IODOPHENYL ETHERS IN FILM-FORMING MATERIALS FOR VISUALIZATION OF THE GASTROINTESTINAL TRACT

[75] Inventors: Carl R. Illig, Phoenixville; Eugene R. Cooper, Berwyn; John L. Toner, Downingtown; Donald A. Upson, West Chester; Brent D. Douty, Coatesville; Thomas J. Caulfield, Audubon, all of Pa.; Bacon, Edward R., East Greenbush, N.Y.; Kimberly G. Estep, Albany, N.Y.; Kurt A. Josef; Shaughnessy Robinson, both of Clifton Park, N.Y.; Paul P. Spara, Fairport, N.Y.

[73] Assignee: Sterling Winthrop Inc., Malvern, Pa.

[*] Notice: The portion of the term of this patent subsequent to Nov. 9, 2010 has been disclaimed.

[21] Appl. No.: 12,171

[22] Filed: Feb. 2, 1993

[51] Int. Cl.[5] .................. A61K 49/04; A61K 31/075
[52] U.S. Cl. .......................................... 424/5; 514/54; 514/57; 514/717; 514/941; 514/942
[58] Field of Search .................. 424/5, 4; 514/54, 57, 514/717, 941, 942; 568/580, 656

[56] References Cited

U.S. PATENT DOCUMENTS

| | | | |
|---|---|---|---|
| 2,348,231 | 5/1944 | Strain et al. | 260/476 |
| 2,622,100 | 12/1952 | Newbery et al. | 260/612 |
| 2,832,722 | 8/1958 | Singher | 167/95 |
| 3,360,436 | 12/1967 | Felder et al. | 167/95 |
| 3,361,700 | 1/1968 | Archer et al. | 260/31.4 |
| 3,574,718 | 4/1971 | Bjork et al. | 260/501.11 |
| 3,795,698 | 3/1974 | Soulal et al. | 260/471 R |
| 3,825,591 | 7/1974 | Felder et al. | 260/519 |
| 4,038,379 | 7/1977 | Elinov et al. | 424/4 |
| 4,069,306 | 1/1978 | Rothman | 424/4 |
| 4,120,946 | 10/1978 | Ouemille et al. | 424/4 |
| 5,019,370 | 5/1991 | Jay et al. | 424/4 |

FOREIGN PATENT DOCUMENTS 1259565 9/1989 Canada .
1481943 5/1967 France .
55-127322 10/1980 Japan .

OTHER PUBLICATIONS

Wang et al. Yaoxne Xuebao 16(8):610–617 (1981).
Janes, A. M. et al. Pharmaceutica Acta Helvetiae 47:244≧256 (1981).

Primary Examiner—Gary E. Hollinden
Attorney, Agent, or Firm—Arthur Rosenstein; Imre Balogh

[57] ABSTRACT

Disclosed are x-ray contrast compositions for oral or retrograde examination of the gastrointestinal tract comprising a polymeric material capable of forming a coating on the gastrointestinal tract and an x-ray producing agent of the formula

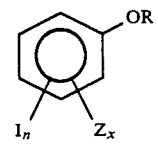

and methods for their use in diagnostic radiology of the gastrointestinal tract wherein Z=H, halo, $C_1$-$C_{20}$ alkyl, cycloalkyl, lower alkoxy, cyano, where the alkyl and cycloalkyl groups can be substituted with halogen or halo-lower-alkyl groups;

R=$C_1$-$C_{25}$ alkyl, cycloalkyl, or halo-lower-alkyl, optionally substituted with halo, fluoro-lower-alkyl, aryl, lower-alkoxy, hydroxy, carboxy, lower-alkoxy carbonyl or lower-alkoxycarbonyloxy, $(CR_1R_2)_p$—$(CR_3=CR_4)_m Q$, or $(CR_1R_2)_p$—C≡C—Q;

$R_1$, $R_2$, $R_3$ and $R_4$ are independently lower-alkyl, optionally substituted with halo;

x is 1–4;
n is 1–5;
m is 1–15;
p is 1–10; and
Q is H, lower-alkyl, lower-alkenyl, lower-alkynyl, lower-alkylene, aryl, or aryl-lower alkyl in a pharmaceutically acceptable carrier.

29 Claims, No Drawings

COMPOSITIONS OF IODOPHENOXY ALKANES AND IODOPHENYL ETHERS IN FILM-FORMING MATERIALS FOR VISUALIZATION OF THE GASTROINTESTINAL TRACT

BACKGROUND OF THE INVENTION

1. Field of the Invention

This invention relates to x-ray contrast compositions containing the contrast agents iodophenoxy alkanes, iodophenyl alkenylalkyl ethers or iodophenyl alkynylalkyl ethers and methods for their use in diagnostic radiology of the gastrointestinal tract.

2. Reported Developments

Roentgenographic examination utilizing X-rays and computed tomography (hereinafter CT) scans of fractures and other conditions associated with the skeletal system is routinely practiced without the use of contrast agents. X-ray visualization of organs containing soft tissue, such as the gastrointestinal (hereinafter GI) tract, requires the use of contrast agents which attenuate X-ray radiation. D. P. Swanson et al in "Pharmaceuticals In Medical Imaging", 1990, MacMillan Publishing Company, provides an excellent background in medical imaging utilizing contrast agents and compositions therewith.

Roentgenographic examination of the GI tract are indicated for conditions of digestive disorders, changes in bowel habit, abdominal pain, GI bleeding and the like. Prior to radiological examination, administration of a radiopaque contrast medium is necessary to permit adequate delineation of the respective lumen or mucosal surface from surrounding soft tissues. Accordingly, a contrast medium is administered orally to visualize the mouth, pharynx, esophagus, stomach, duodenum and proximal small intestine. The contrast medium is administered rectally for examination of the distal small intestine and the colon.

The most widely used contrast agent for the visualization of the GI tract is barium sulfate administered as a suspension orally or rectally as an enema. (See, for example, U.S. Pat. Nos.: 2,659,690; 2,680,089; 3,216,900; 3,235,462; 4,038,379 and 4,120,946) Notwithstanding its relatively good contrast characteristics, negligible absorption from the GI tract following oral or rectal administration and speedy excretion from the body, barium sulfate has certain disadvantages. In the presence of intestinal fluids it lacks homogeneity and poorly adheres to mucus membranes which can result in poor X-ray images. In the colon, when administered as an enema, it flocculates and forms irregular clumps with fecal matter.

Iodinated organic compounds have also been used as GI contrast agents since the iodine atom is an effective X-ray absorber. They have the most versatility and are utilized in the widest variety of procedures. They are very absorptive of X-rays with which the iodine interacts and produce a so-called photoelectric effect which is a large magnification in contrast caused by the photons stopped in the iodine-containing medium. The magnification of contrast exceeds the level that would be expected from relative changes in density. Because of this magnification, relatively low concentrations of the contrast agent can be utilized. (For iodinated agents see, for example, U.S. Pat. Nos.: 2,786,055; 3,795,698; 2,820,814; 3,360,436; 3,574,718; 3,733,397; 4,735,795 and 5,047,228.)

The desiderata for an ideal GI contrast agent includes: good toxicological profile; the ability to fill the entire bowel/lumen and evenly coat the gut mucosa so that the presence of the bowel is detectable when the lumen is not distended; and nonirritation to the intestinal mucosa; and passage through the GI tract without producing artifacts or stimulating vigorous intestinal peristalsis.

These requirements were addressed by many investigators and their efforts resulted in great improvements over the years. The requirement of evenly coating the gut mucosa with a contrast agent to effectively cover the walls of the intestines proved to be rather difficult. Without meeting these requirements it is impossible to obtain X-ray pictures of high precision. To that end, the use of certain polymer additives were proposed as illustrated hereunder.

U.S. Pat. No. 4,069,306 discloses an X-ray contrast preparation which is said to adhere to the walls of body cavities. The preparation comprises a finely divided water-insoluble inorganic X-ray contrast agent and minute particles of a hydrophilic polymer which is insoluble in water but is water-swellable. The body cavity is supplied with such preparation suspended in water. The X-ray contrast agent is present in admixture with and/or enclosed in and/or adhered to said minute polymer particles.

U.S. Pat. No. 4,120,946 discloses a pharmaceutical composition for barium opacification of the digestive tract, comprising colloidal barium sulfate and a polyacrylamide in an aqueous vehicle. The polyacrylamide forms a viscous solution at low concentration which makes it possible to maintain the barium sulfate in suspension and at the same time permit good adherence of the preparation to the walls of the organ which it is desired to X-ray.

U.S. Pat. No. 5,019,370 discloses a biodegradable radiographic contrast medium comprising biodegradable polymeric spheres which carry a radiographically opaque element, such as iodine, bromine, samarium and erbium. The contrast medium is provided either in a dry or liquid state and may be administered intravenously, orally and intra-arterially.

While these polymeric materials greatly enhance attachment of the contrast agent used therewith to the walls of organs for better visualization thereof, they do not provide a uniform coating thereon. As such, there is still a need for an improved X-ray imaging medium that uniformly coats the soft tissues subjected to diagnostic X-ray examination.

SUMMARY OF THE INVENTION

It is the object of the present invention to provide compositions for coating the gastrointestinal tract of mammals to form an effective radiopaque coating thereon by which diagnostic examination of the GI tract may be accomplished. To that end, a thin coating is formed on the inner surface of the GI tract effected by ingesting, prior to visualization by an X-ray emitting device, a polymeric film former, which has incorporated therein an X-ray contrast agent, capable of coating the GI tract. The removal of the coating occurs as a result of the normal turnover of cells, that is, within about 24 to 48 hours. Such compositions must meet several requirements: both the X-ray contrast agent and the film former must be nontoxic; must not contain leachable or digestible components that would deleteriously affect the patient; and the composition must be capable of forming a film in the pH range of from about 5 to about 8.

The object of the present invention is achieved by a composition comprising: an X-ray contrast agent; a polymeric material which is at least partially water soluble and contains polarizable or ionizable groups; and a divalent metal ion selected from the group consisting of $Mg^{++}$, $Ca^{++}$, $Zn^{++}$ and $Ba^{++}$ which potentiates the effect of the polymeric material as a film former on the mucosa of the GI tract.

The contrast agent, polymeric film former and the divalent metal ion are incorporated in a solid or liquid media for administration to a mammal for X-ray visualization of the GI tract.

In accordance with the invention there is further provided a method for x-ray diagnostic imaging of the GI tract which comprises orally or rectally administering to the patient an effective contrast producing amount of one of the above-described x-ray contrast compositions.

The composition for radiological examination of the GI tract comprises a compound of the formula:

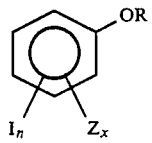

or a pharmaceutically acceptable salt thereof wherein
Z=H, halo, $C_1$-$C_{20}$ alkyl, cycloalkyl, lower alkoxy, cyano, where the alkyl and cycloalkyl groups can be substituted with halogen or halo-lower-alkyl groups;
R=$C_1$-$C_{25}$ alkyl, cycloalkyl, or halo-lower-alkyl, optionally substituted with halo, fluoro-lower-alkyl, aryl, lower-alkoxy, hydroxy, carboxy, lower-alkoxy carbonyl or lower-alkoxycarbonyloxy, $(CR_1R_2)_p$—$(CR_3$=$CR_4)_mQ$, or $(CR_1R_2)_p$—$C$≡$C$—$Q$;
$R_1$, $R_2$, $R_3$ and $R_4$ are independently lower-alkyl, optionally substituted with halo;
x is 1-4;
n is 1-5;
m is 1-15;
p is 1-10; and
Q is H, lower-alkyl, lower-alkenyl, lower-alkynyl, lower-alkylene, aryl, or aryl-lower alkyl.

As used herein, the term halogen (or halo) means fluorine, chlorine, bromine or iodine.

As used herein, the term cycloalkyl means carbocyclic rings having from three to eight ring carbon atoms including cyclopropyl, cyclobutyl, cyclopentyl, cyclohexyl and cyclooctyl which may be substituted on any ring carbon atom thereof by one or more lower-alkyl groups, lower-alkoxy groups or halogens.

As used herein the terms lower-alkyl and lower-alkoxy mean monovalent aliphatic radicals, including branched chain radicals, of from one to ten carbon atoms. Thus, the lower-alkyl moiety of such groups include, for example, methyl, ethyl, propyl, isopropyl, n-butyl, sec-butyl, t-butyl, n-pentyl, 2-methyl-3-butyl, 1-methylbutyl, 2-methylbutyl, neopentyl, n-hexyl, 1-methylpentyl, 3-methylpentyl, 1-ethylbutyl, 2-ethylbutyl, 2-hexyl, 3-hexyl, 1,1,3,3-tetramethylpentyl, 1,1-dimethyloctyl and the like.

As used herein, the term lower-alkenyl and lower-alkynyl means monovalent, unsaturated radicals including branched chain radicals of from three to ten carbon atoms and thus include 1-ethenyl, 1-(2-propenyl), 1-(2-butenyl), 1-(1-methyl-2-propenyl), 1-(4-methyl-2-pentenyl), 4,4,6-trimethyl-2-heptenyl, 1-ethynyl, 1-(2-propynyl), 1-(2-butynyl), 1-(1-methyl-2-propynyl), 1-(4-methyl-2-pentynyl) and the like.

As used herein, the term alkylene means divalent saturated radicals, including branched chain radicals of from two to ten carbon atoms having their free valences on different carbon atoms and thus includes 1,2-ethylene, 1,3-propylene, 1,4-butylene, 1-methyl-1,2-ethylene, 1,8-octylene and the like.

As used herein, the term aryl means an aromatic hydrocarbon radical having six to ten carbon atoms. The preferred aryl groups are phenyl, substituted phenyl and naphthyl substituted by from one to three, the same or different members of the group consisting of lower-alkyl, halogen, hydroxy-lower-alkyl, alkoxy-lower-alkyl and hydroxy.

The x-ray contrast compound can comprise one, two, three or more iodine atoms per molecule; preferred species contain at least two, and more preferably, at least three iodine atoms per molecule.

The solid x-ray contrast agents in particulate forms useful in the practice of the present invention can be prepared by techniques known in the art. The solid agents are comminuted to the desired size using conventional milling methods, such as airjet or fragmentation milling. We have found that an effective average particle size of less than about 100μ provides for good distribution and coating in the GI tract. As used herein, particle size refers to a number average particle size as measured by conventional techniques, such as sedimentation field flow fractionation and disk centrifugation. An effective average particle size of less than about 100μ means that at least about 90% of the particles have a weight average particle size of less than about 100μ as measured by art recognized techniques.

The polymers that were found to be suitable for forming a thin coating on the GI tract can be classified as anionic, cationic and neutral polymers, a description of which follows. U.S. Pat. No. 4,623,539, the disclosure of which is incorporated by reference, pertains to such polymers.

The contrast agent is incorporated in the polymeric material along with the divalent cation by any suitable techniques, such as by mixing, blending, precipitating or by enclosing the contrast agent into minute polymeric particles.

The contrast agent, polymeric material and divalent cation blend is then formulated for administration using physiologically acceptable carriers or excipients in a manner within the skill of the art. The contrast agent with the addition of pharmaceutically acceptable aids (such as surfactants and emulsifiers) and excipients may be suspended or partially dissolved in an aqueous medium resulting in a dispersion, solution, suspension or emulsion. Alternatively, the contrast agent, polymeric material and divalent cation may be formulated into a solid form, such as tablets or capsules.

A method for diagnostic imaging of the GI tract for use in medical procedures in accordance with this invention comprises orally or rectally administering to the mammalian patient in need of x-ray examination, an effective contrast producing amount of a composition of the present invention. After administration, at least a portion of the GI tract containing the administered composition is exposed to x-rays to produce an x-ray image pattern corresponding to the presence of the contrast agent, then the x-ray image is visualized and interpreted using techniques known in the art.

DETAILED DESCRIPTION OF THE INVENTION

Compounds of the present invention can be made according to the schematic procedure shown or other methods using commercially available starting materials, intermediates and reagents. Starting materials, reagents and solvents can be obtained from chemical suppliers such as Aldrich, Baker and Eastman Chemical Companies, or they may be prepared by techniques known in the art.

Scheme 1

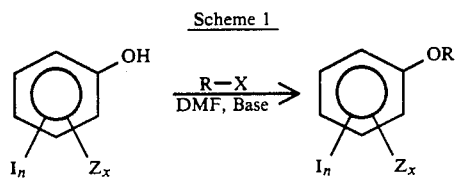

wherein X = Halogen, $OSO_2CH_3$
x = 1–4
Z and R are as described above.

Scheme 2

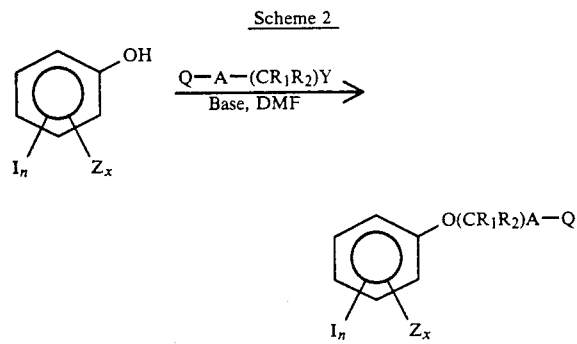

wherein A = $-(CR_3=CR_4)_m-$
$-C\equiv C-$
Y = Halogen, $OSO_2CH_3$
x = 1–4
and $I_n$, Z, $R_1$, $R_2$, $R_3$, $R_4$ and Q
are as described above.

The following examples will further illustrate the compounds used in the present invention.

EXAMPLE 1

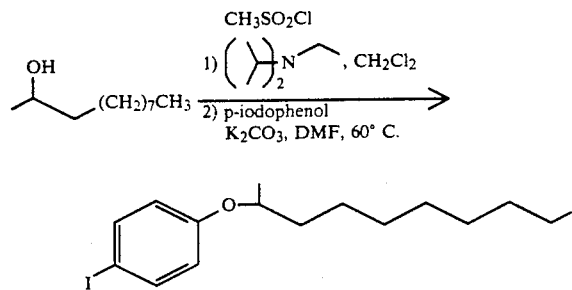

To a solution of 2-decanol (5.0 ml, 26.0 mmol) in dry $CH_2Cl_2$ (52 ml) under an $N_2$ atmosphere was added diisopropylethylamine (5.6 ml, 32.1 mmol). The reaction flask was immersed in an ice/water bath. After stirring for 10 minutes, methanesulfonyl chloride (2.8 ml, 36.1 mmol) was added via syringe over a period of 10 minutes. After stirring for 3 hrs, the reaction was diluted with cold $CH_2Cl_2$ (200 ml) and poured into cold 5% aqueous HCl (100 ml). The layers were separated and the organic phase washed with cold 5% aqueous HCl (50 ml) followed by brine (2×50 ml). The $CH_2Cl_2$ layer was dried ($Na_2SO_4$), filtered and evaporated in vacuo at 25° C. The resulting light yellow oil was pumped under reduced pressure for 2 hrs to provide 2-methanesulfonyloxydecane (6.5 g, 93.5%) as a light yellow oil.

Without further purification, the above product (6.5 g, 24.3 mmol) was dissolved in 50 ml dry N,N-dimethylformamide (DMF) with stirring. 4-Iodophenol (4.8 g, 21.8 mmol) and potassium carbonate (3.4 g, 24.6 mmol) were then added to the reaction flask which was immersed in an oil bath and heated to 57° C. over a period of 0.5 hr. After stirring for 14 hrs under an $N_2$ atmosphere at 57° C., $^1H$ NMR spectral analysis indicated about half of the mesylate was present. The temperature of the oil bath was increased to 66° C. and stirring continued. After an additional 21 hrs, $^1H$ NMR spectral analysis indicated that less than 5% of the mesylate remained. After stirring for a total of 37 hrs, the reaction was allowed to cool and filtered through a pad of celite with washings of DMF to a total volume of 250 ml. The DMF layer was extracted with hexanes (3×100 ml) and then diluted with 0.1M aqueous sodium hydroxide. (250 ml). The mixed DMF/aqueous phase was extracted with hexanes (2×100 ml). The combined hexane washings were washed successively with 1M aqueous sodium hydroxide (2×200 ml), water (2×200 ml) and brine (2×200 ml), dried ($Na_2SO_4$), filtered, and evaporated in vacuo to provide a light yellow oil. This product was further purified by flash column chromatography (silica, hexanes) to yield 2-(4-iodophenoxy)-decane (4.05 g, 51.6%) as a clear oil. Title Compound: $^1H$ (300 MHz) and $^{13}C$ (75 MHz) NMR spectra were consistent with the desired structure. FAB/MS: M+, 360. Calculated for $C_{16}H_{25}IO$: C, 53.34; H, 6.99; I, 35.22. Found: C, 53.47, H, 6.99; I, 35.43.

EXAMPLE 2

2-(2,4,6-Triiodophenoxy)-pentadecane

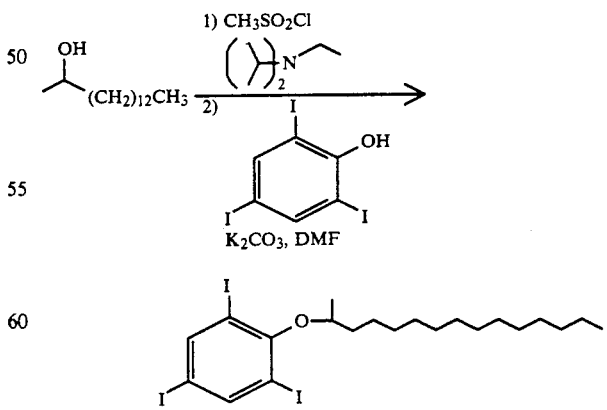

The 2-methanesulfonyloxypentadecane was prepared as follows: the mesylate of 2-pentadecanol was prepared from 2-pentadecanol (25 g, 109 mmol), methanesulfonylchloride (11.8 ml, 152 mmol) and diisopropylethylamine (22.8 ml, 131 mmol) as previously described in 95% yield.

To a solution of 2-methanesulfonyloxypentadecane (15.5 g, 48.1 mmol) in dry DMF (200 ml) was added triiodophenol (22.6 g, 47.9 mmol) and potassium carbonate (6.6 g, 47.8 mmol). The reaction flask was immersed in an oil bath which was heated to 85° C. over a period of 0.5 hr. The reaction was stirred under $N_2$ atmosphere for 16 hrs. At the end of this period the reaction was processed as for Example 1 except at 4 times the volumes to provide a brown residue. Flash column chromatography (silica, hexanes) provided 2-(2,4,6-triiodophenoxy)pentadecane (19.2 g, 58.8%) as a white solid. Mp: 56°–58° C. Title Compound: $^1$H (300 MHz) and $^{13}$C (75 MHz) NMR spectra were consistent with the desired structure. Calculated for $C_{21}H_{33}I_3O$: C, 36.97; H, 4.88; I, 55.81. Found: C, 36.89, H, 4.80; I, 55.85.

EXAMPLE 3

2-(2,4,6-Triiodophenoxy)decane

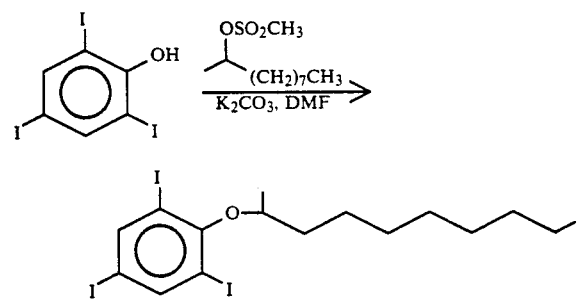

The 2-methanesulfonyloxydecane (14.8 g, 62.6 mmol), 2,4,6-triiodophenol (29.7 g) 62.9 mmol) and potassium carbonate (8.7 g, 63.0 mmol) were reacted in DMF (210 ml) as per 2-(2,4,6-triiodophenoxy)-pentadecane except at an oil bath temperature of 72° C. for 88 hrs. The reaction was processed as for 2-(2,4,6-triiodophenoxy)-pentadecane to provide a light brown residue. Flash column chromatography (silica, hexanes) provided 2-(2,4,6-triiodophenoxy)-decane (29.1 g, 75.9%) as a white solid. Title Compound: $^1$H (300 MHz) and $^{13}$C (75 MHz) NMR spectra were consistent with the desired structure. Calculated for $C_{16}H_{23}I_3O$: C, 31.40; H, 3.79; I, 62.20. Found: C, 31.50, H, 3.75; I, 62.37.

EXAMPLE 4

(2,4,6-Triiodophenoxy)-1H, 1H, 2H, 2H-perfluorooctane

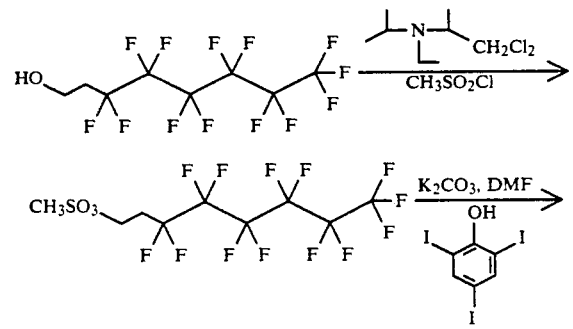

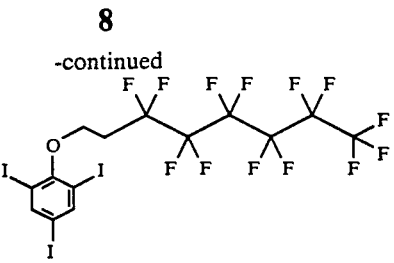

A mixture of 3.00 g (8.24 mmol) of 1H, 1H, 2H, 2H-perfluorooctanol and 1.28 g (9.89 mmol) of N,N-diisopropylethylamine in 12 ml of dry dichloromethane was placed under nitrogen and cooled to 0° C. Methanesulfonyl chloride (1.04 g, 9.06 mmol) was added dropwise via syringe and the resulting solution was stirred at 0° C. for 1.5 hrs. The mixture was partitioned between 100 ml of dichloromethane and 100 ml of 1M HCl. The dichloromethane layer was then washed with water (100 ml) and brine (100 ml). The solution was dried over $Na_2SO_4$ and concentrated in vacuo to afford 3.28 g (90%) of the mesylate as a white solid.

A mixture of 2.11 g (4.77 mmol) of the above mesylate, 1.50 g (3.18 mmol) of 2,4,6-triiodophenol and 0.75 g (5.41 mmol) of potassium carbonate in 5 ml of dry DMF was stirred and heated to 80° C. under nitrogen for 40 hrs. The mixture was cooled and partitioned between 100 ml of ethyl acetate and 100 ml of 1M HCl. The ethyl acetate layer was then washed with water (50 ml) and brine (25 ml). The brown solution was dried over $Na_2SO_4$ and concentrated in vacuo to yield a brown solid (1.89 g). The brown solid purified by flash chromatography (silica gel, hexanes) affording 1.35 g (52%) of the pure product. Mp: softens at 55°–58° C., melts at 63° C. Title Compound: $^1$H (300 MHz) and $^{13}$C (75 MHz) NMR spectra were consistent with the desired structure. FAB/MS: $(M+1)^+$ 818. Calculated for $C_{14}H_6F_{13}I_3O$: C, 20.56; H, 0.74. Found: C, 20.75; H, 0.69.

EXAMPLE 5

1-(2,4,6-Triiodo-3-trifluorophenoxy)octane

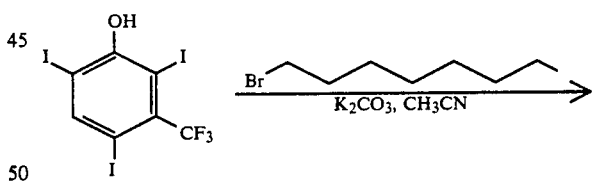

A mixture of 0.540 g (1.00 mmol) of 2,4,6-triiodo-3-trifluoromethyl phenol, 0.691 g (5.00 mmol) of potassium carbonate and 0.212 g (1.10 mmol) of 1-bromooctane in 3 ml of dry acetonitrile was heated to reflux under nitrogen and stirred for 3.5 hrs. The mixture was cooled and partitioned between 50 ml of water and 75 ml of ethyl acetate. The ethyl acetate layer was then washed with brine (20 ml), dried over $Na_2SO_4$ and concentrated in vacuo to 0.645 g of yellow oil. The oil was purified by flash chromatography on 25 g of silica gel with hexane as the eluent to give 0.498 g (76%) of a colorless oil which crystallized to a white solid on standing. Mp. 39°–42° C. Title Compound: $^1$H (300 MHz) and $^{13}$C (75 MHz) NMR spectra were consistent with the desired structure. FAB/MS: (M−1)+ 651. Calculated for $C_{15}H_{18}F_3I_3O$: C, 27.63; H, 2.78; I, 58.34. Found: C, 28.11; H, 2.78; I, 57.11.

EXAMPLE 6

2-(2,4,6-Triiodophenoxy)-nonane

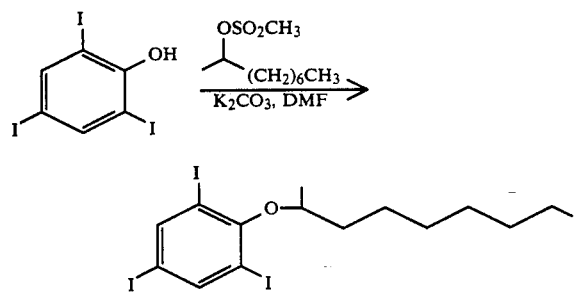

The 2-methanesulfonyloxynonane (22.8 g, 102 mmol), triiodophenol (48.8 g, 103 mmol) and potassium carbonate (14.2 g, 103 mmol) were reacted in DMF (206 ml) as per 2-(2,4,6-triiodophenoxy)pentadecane except at an oil bath temperature of 82° C. for 14 hrs. The reaction was processed as for 2-(2,4,6-triiodophenoxy)-pentadecane to provide a light brown oil. Flash column chromatography (silica, hexanes) provided 2-(2,4,6-triiodophenoxy)nonane (40.8 g, 68.0%). Title Compound: $^1$H (300 MHz) and $^{13}$C (75 MHz) NMR spectra were consistent with the desired structure. Calculated for $C_{15}H_{21}I_3O$: C, 30.13; H, 3.54; I, 63.66. Found: C, 30.52, H, 3.49; I, 63.47.

EXAMPLE 7

2-Ethyl-1-(2,4,6-triiodophenoxy)-hexane

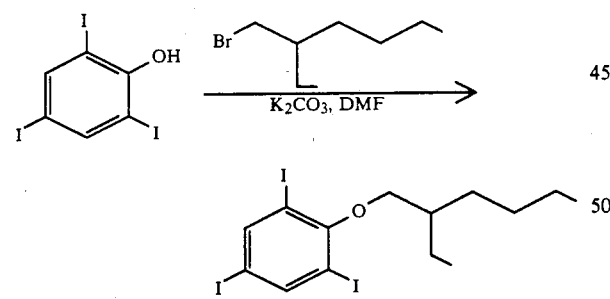

2-Ethyl-bromohexane (10.4 g, 53.0 mmol), triiodophenol (25.5 g, 54.0 mmol) and potassium carbonate (7.5 g, 54.3 mmol) were reacted in dry DMF (110 ml) at 77° C. as for 2-(2,4,6-triiodophenoxy)butane. After stirring for 20 hrs, the reaction was cooled, diluted with DMF, filtered through a pad of celite and evaporated in vacuo. The resulting residue was taken up in EtOAc (500 ml), washed with water (200 ml), 1N aqueous sodium hydroxide (200 ml), water (2×200 ml) and brine (200 ml), dried (Na$_2$SO$_4$), filtered and evaporated. Flash column chromatography (silica, hexanes) provided 2-ethyl-1-(2,4,6-triiodophenoxy)-hexane (22.8 g, 73.7%) as a clear viscous oil. Title Compound: $^1$H (300 MHz) and $^{13}$C (75 MHz) NMR spectra were consistent with the desired structure. Calculated for $C_{14}H_{19}I_3O$: C, 28.79; H, 3.28; I, 65.19. Found: C, 29.13, H, 3.24; I, 65.05.

EXAMPLE 8

3,3-Diphenyl-1-(2,4,6-triiodophenoxy)propane

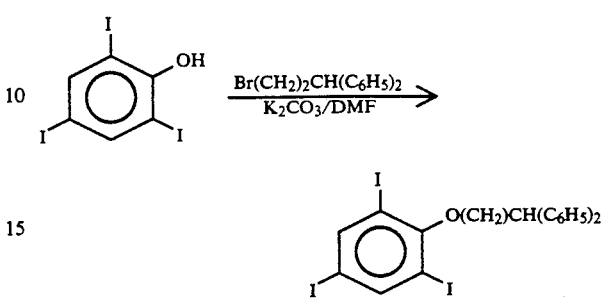

A mixture of 2,4,6-triiodophenol (0.78 g, 1.65 mmol) and potassium carbonate (0.25 g, 1.82 mmol, 1.1 eq) in 5 ml of dimethylformamide was heated at 60° C. for 1 hr, cooled and then 3,3-diphenylpropyl bromide (0.5 g, 1.82 mmol) was added. After stirring for 30 minutes at room temperature the mixture was heated at 60° C. for 24 hrs. The mixture was then cooled, poured into water and the crude product was isolated by ethyl acetate extraction. The product was purified by silica gel chromatography (2.5% ethyl acetate-hexanes) followed by recrystallization from hexanes to give 0.53 g (48%) of a solid. Mp: 120°–121° C. Title Compound: $^1$H (300 MHz) and $^{13}$C (75 MHz) NMR spectra were consistent with the desired structure. Calculated for $C_{21}H_{17}I_3O$: C, 37.87; H, 2.57; I, 57.66. Found: C, 37.95; H, 2.60; I, 57.11.

EXAMPLE 9

3-(2,4,6-Triiodophenoxy)-nonane

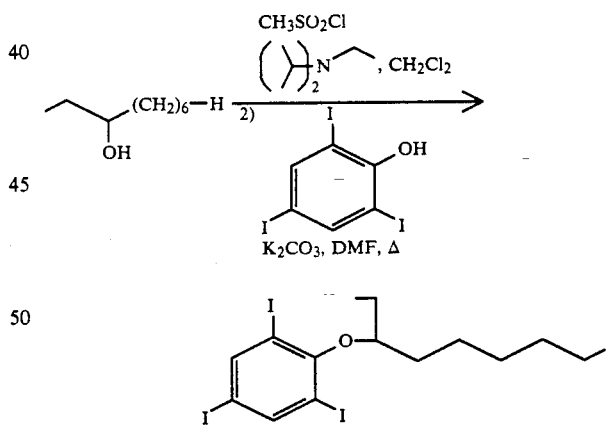

The mesylate of 3-nonanol was prepared in the usual manner form 3-nonanol (7.5 g, 52 mmol), diisopropyl ethylamine (11.7 ml, 67 mmol) and methane sulfonyl chloride (4.8 ml, 62 mmol) in dry CH$_2$Cl$_2$ (104 ml).

The mesylate of 3-nonanol (11.5 g, 51.9 mmol), triiodophenol (24.5 g, 51.9 mmol) and potassium carbonate (7.18 g, 51.9 mmol) were reacted in dry DMF (200 ml) as per 2-(2,4,6-triiodophenoxy)-pentadecane except at an oil bath temperature of 87° C. for 16 hrs. The reaction was processed as for 2-(2,4,6-triiodophenoxy)-pentadecane to provide a light brown oil. Flash column chromatography (silica, hexanes) provided 3-(2,4,6-Triiodophenoxy)-nonane (20.9 g, 67%) as a clear viscous oil. Title Compound: $^1$H (300 MHz) and $^{13}$C (75 MHz) NMR spectra were consistent with the desired structure. FAB/MS M+ 598. Calculated for $C_{15}H_{21}I_3O$: C, 30.13; H, 3.54; I, 63.66. Found: C, 30.54, H, 3.51; I, 63.58.

EXAMPLE 10

2-(4-Iodophenoxy)-undecane

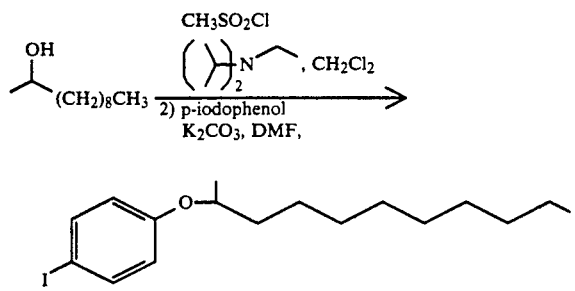

2-Methanesulfonyloxyundecane was prepared as described for 2-methanesulfonyloxydecane from 2-undecanol (30.0 ml, 144 mmol), methanesulfonylchloride (15.5 ml, 200 mmol) and diisopropylethylamine (30.8 ml, 177 mmol) in dry $CH_2Cl_2$ (240 ml). After stirring for 3.5 hrs, the reaction was processed as previously stated but at 4 times the volumes to provide 2-methanesulfonyloxyundecane (31.35 g, 95%).

The above product (31.3 g, 136.7 mmol) was reacted with 4-iodophenol (30.1 g, 136.8 mmol), and potassium carbonate (18.9 g, 136.7 mmol) in DMF (270 ml) at 80° C. as for 2-(4-iodophenoxy)decane. After stirring for 13 hrs, the reaction was analyzed by $^1$H NMR indicating that the reaction was about 66% complete. The temperature of the oil was increased 84° C. After an additional 34 hrs, $^1$H NMR spectral analysis indicated that the reaction was complete. The reaction was processed as for 2-(4-iodophenoxy)-decane except at 2 times the volume to give a light yellow oil. This product was further purified by flash column chromatography (silica, hexanes) to give 2-(4-iodophenoxy)-undecane (16.1 g, 31%) as a clear oil. Title Compound: $^1$H (300 MHz) and $^{13}$C (75 MHz) NMR spectra were consistent with the desired structure. FAB/MS: M+, 374. Calculated for $C_{17}H_{27}IO$: C, 54.55; H, 7.27; I, 33.90. Found: C, 54.75, H, 7.32; I, 33.97.

EXAMPLE 11

2-Iodophenoxycyclopentane

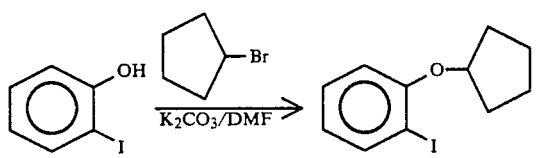

A mixture of 2-iodophenol (8.0 g, 36.4 mmol), milled potassium carbonate (5.5 g, 39.9 mmol, 1.1 eq) and 1-bromocyclopentane bromide (3.9 ml, 36.4 mmol) in 25 ml of N,N-dimethylformamide was heated at 120° C. for 1.1 hrs and cooled. The mixture was poured into water and extracted twice with ether. The ether layer was dried over magnesium sulfate, filtered, and concentrated to give an oil. The crude product was dissolved in ethyl acetate and filtered through a short pad of silica gel. The filtrate was redried over magnesium sulfate, filtered and concentrated under vacuum to give 10 g (95%) of product as an oil. Title Compound: $^1$H (300 MHz) and $^{13}$C (75 MHz) NMR spectra were consistent with the desired structure. Calculated for $C_{11}H_{13}IO$: C, 45.85; H, 4.55; I, 44.04. Found: C, 45.78; H, 4.51; I, 43.88.

EXAMPLE 12

3-Iodophenoxycyclopentane

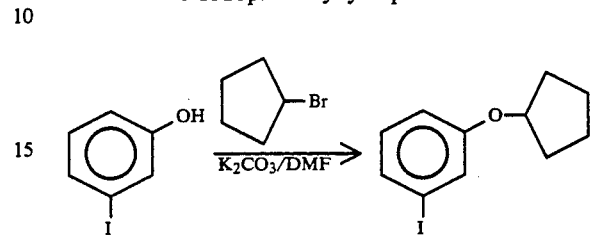

Using the same procedure as in the preparation of 2-iodophenoxycyclopentane, 3-iodophenoxycyclopentane was prepared in 68% yield from 3-iodophenol (9.9 g, 45.4 mmol), potassium carbonate (6.9 g, 49.9 mmol, 1.1 eq) and cyclopentyl bromide (5.4 ml, 49.9 mmol, 1.1 eq). The crude product was isolated by ethyl acetate extraction and filtration through a pad of basic alumina affording the pure product as an oil after concentration under high vacuum. Title Compound: $^1$H (300 MHz) and $^{13}$C (75 MHz) NMR spectra were consistent with the desired structure. Calculated for $C_{11}H_{13}IO$: C, 45.85; H, 4.55; I, 44.04. Found: C, 46.03; H, 4.46; I, 44.12.

EXAMPLE 13

(3,5-Dimethyl-2,4,6-triodophenoxy)cyclopentane

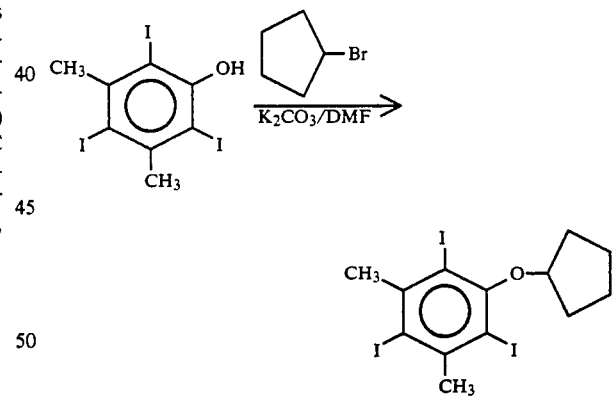

A mixture of 3,5-dimethyl-2,4,6-triiodophenol (4.0 g, 8 mmol), cyclopentyl bromide (1.0 ml, 9.6 mmol, 1.2 eq), and potassium carbonate (1.33 g, 9.6 mmol, 1.2 eq.) in N,N-dimethylformamide (30 ml) was stirred at room temperature overnight. The mixture was poured into water and extracted first with ethyl acetate and then dichloromethane. The combined organic extracts were dried over magnesium sulfate and stripped to give a gum. The crude product was dissolved in ethyl acetate and filtered through a pad of silica gel and then through a pad of basic alumina. The filtrates were combined, concentrated and the product was then isolated (56% yield) by silica gel chromatography (hexanes) to give a viscous oil which solidified under high vacuum. Mp. 68°–80° C. Title Compound: $^1$H (300 MHz) and $^{13}$C (75

MHz) NMR spectra were consistent with the desired structure. Calculated for $C_{13}H_{15}I_3O$: C, 27.49; H, 2.66; I, 67.03. Found C, 27.76; H, 2.62; I, 65.65.

EXAMPLE 14

2-(4-Iodophenoxy)-pentadecane

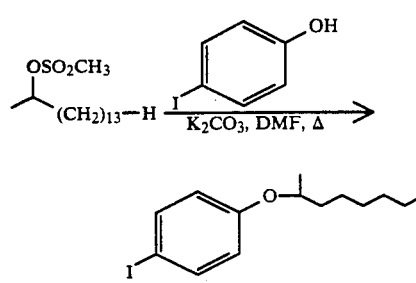

The 2-methanesulfonyloxypentadecane was prepared from 2-pentadecanol (25 g, 109 mmol), methanesulfonylchloride (11.8 ml, 152 mmol) and diisopropylethylamine (22.8 ml, 131 mmol) as previously described in 95% yield.

The 2-methanesulfonyloxypentadecane (34.4 g, 102 mmol) was reacted with 4-iodophenol (22.7 g, 103 mmol) and potassium carbonate (14.3 g, 103 mmol) in DMF (200 ml) as per 2-(4-iodophenoxy)decane except that the temperature of the oil bath was maintained at 80° C. for 15 hrs and increased to 86° C. with stirring for an additional 24 hrs. At the end of this period, NMR spectral analysis indicated that the reaction was complete. The reaction mixture was processed as for 2-(4-iodophenoxy)decane except with four times the volumes to provide a light yellow oil. Flash column chromatography (silica, hexanes) yielded 2-(4-iodophenoxy)pentadecane (18.9 g, 43.0%) as a clear oil. Title Compound: $^1H$ (300 MHz) and $^{13}C$ (75 MHz) NMR spectra were consistent with the desired structure. FAB/MS: M+, 430. Calculated for $C_{21}H_{35}IO$: C, 58.47; H, 8.41; I, 29.42. Found: C, 58.91, H, 8.36; I, 29.26.

EXAMPLE 15

4-Iodophenoxycyclopentane

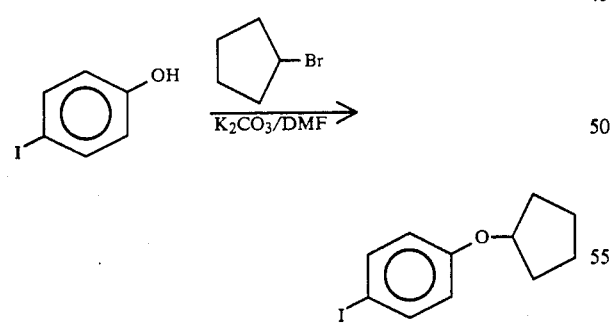

Using the procedure described for 2-iodophenoxycyclopentane, 4-iodophenoxycyclopentane was prepared in 80% yield from 4-iodophenol (4.0 g, 18.2 mmol), cyclopentyl bromide (1.95 ml, 18.2 mmol, 1 eq) and potassium carbonate (2.76 g, 20 mmol, 1.1. eq) in 25 ml of dimethylformamide after ether extraction and filtration through basic alumina. The pure product was obtained as a solid (mp 50°-52° C.) after crystallization from hexanes. Title Compound: $^1H$ (300 MHz) and $^{13}C$ (75 MHz) NMR spectra were consistent with the desired structure. Calculated for $C_{11}H_{13}IO$: C, 45.85; H, 4.55; I, 44.04. Found: C, 45.90; H, 4.48; I, 44.13.

EXAMPLE 16

2,4,6-Triiodophenoxycyclopentane

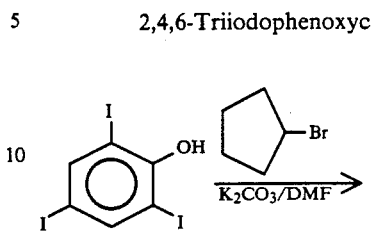

Milled, anhydrous potassium carbonate (14.2 g, 103 mmol, 1.2 eq) was added in portions to a stirred solution of 2,4,6-triiodophenol (40.5 g, 85.8 mmol) in 50 ml of dry (4A sieves) dimethylformamide at room temperature. After stirring for 20 minutes, cyclopentyl bromide (12 ml, 112 mmol, 1.3 eq) in dimethylformamide (20 ml) was added and the viscous mixture was gradually heated to 130° C. under argon for approximately 45 minutes. After cooling, the mixture was filtered and the collected solid was washed with chloroform. The filtrate was concentrated in vacuo to give 50 g of an amber oil. The crude oily product was partitioned between ethyl acetate (300 ml) and water (500 ml); the organic layer was dried over magnesium sulfate and passed through a short pad of silica gel. The filtrate was treated with decolorizing carbon, filtered, and stripped to give an amber oil. The oil was dried at 60° C. under high vacuum to give 40.4 g (87%) of product. Title Compound: $^1H$ (300 MHz) and $^{13}C$ (75 MHz) NMR spectra were consistent with the desired structure. MS: M+ 540; Calculated for $C_{11}H_{11}I_3O$: C, 24.47; H, 2.05; I, 70.51. Found: C, 24.42; H, 1.98; I, 70.58.

EXAMPLE 17

2,4,6-Triiodophenoxymethylcyclopentane

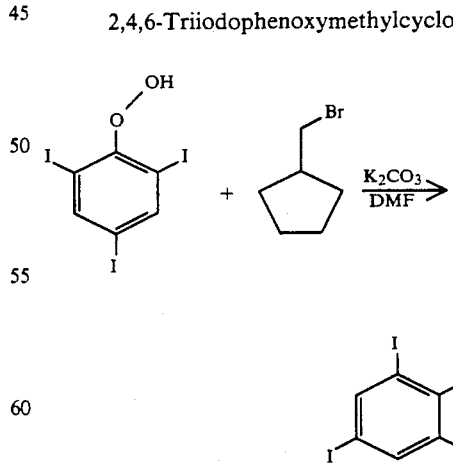

A stirred mixture of 36.2 g (0.08 mol) of 2,4,6-triiodophenol, 12.5 g (0.08 mol) of bromomethylcyclopentane [Noller and Adams, J. Org. Chem., 48, 1080–9 (1926)] and 10.6 g (0.08 mol) of milled anhydrous potassium carbonate in 100 ml dry dimethylformamide was heated at 100° C. under argon for 3.5 hrs. The mixture was cooled and concentrated in vacuo. The resulting residue was combined with 100 ml of ice-cold water and the oily product was extracted with ethyl acetate (3×100 ml). The combined ethyl acetate extracts were dried (MgSO4) and concentrated in vacuo to a dark oil. The oil was purified by chromatography (neutral alumina eluted by hexanes) to yield 24.0 g (57%) of the desired product as an oil. Bp: 220°-5° C./1 atm. Title Compound: $^1$H (300 MHz) and $^{13}$C (75 MHz) NMR spectra were consistent with the desired structure. FAB/MS: M+ 553; Calculated for $C_{12}H_{13}I_3O$: C, 26.02; H, 2.37; I, 68.73. Found: C, 26.33; H, 2.37; I, 68.47.

EXAMPLE 18

2-(2,4,6-Triiodophenoxy)ethylcyclopentane

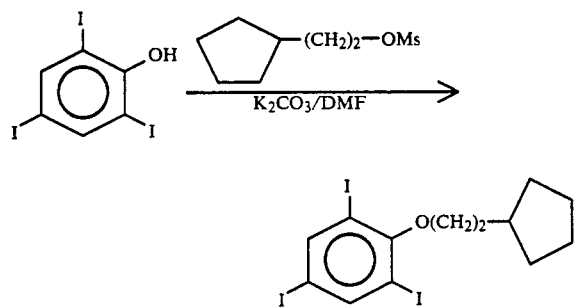

Methanesulfonyl chloride (2.72 ml, 35.1 mmol, 1.1 eq) was added dropwise over a period of several minutes to a cooled (ice/methanol) and stirred solution of 2-cyclopentylethanol (3.64 g, 31.9 mmol) and triethylamine (6.23 ml, 47.9 mmol, 1.5 eq) in 200 ml of dry (4 A molecular sieves) dichloromethane under an argon atmosphere. After stirring for several minutes, a white precipitate formed and the mixture was stirred an additional 30 minutes. The reaction mixture was washed successively with water, 10% aqueous hydrochloric acid, saturated aqueous sodium bicarbonate, saturated sodium chloride and then dried over magnesium sulfate. The organic layer was filtered and concentrated under vacuum to give 5.87 g (95%) of the methanesulfonate ester as a pale yellow liquid which was stored in the cold and used without further purification. $^1$H-NMR (300 MHZ) spectral data was consistent with the desired product. CI/MS: M+ 193.

To a stirred mixture of 2,4,6-triiodophenol (20.36 g, 43.2 mmol) and milled anhydrous potassium carbonate (7.2 g, 52.2 mmol) in 75 ml of dry dimethylformamide was added dropwise over 10 minutes, a solution of 2-cyclopentylethylmethanesulfonate (8.2 g, 42.7 mmol) in 10 ml of dimethylformamide. The mixture was heated at 65° C. under argon overnight and the solvent was then removed under vacuum. The resulting amber residue was partitioned between ethyl acetate (200 ml) and water (30 ml). The aqueous layer was further extracted with ethyl acetate (2×250 ml) and the combined ethyl acetate extracts were treated with decolorizing carbon, dried over magnesium sulfate and passed through a short pad of basic alumina. The filtrate was evaporated under vacuum to give 17.5 g (73%) of the desired product as an amber oil. Title Compound: $^1$H (300 MHz) and $^{13}$C (75 MHz) NMR spectra were consistent with the desired structure. FAB/MS: M+ 568; Calculated for $C_{13}H_{15}I_3O$: C, 27.49; H, 2.66; I, 67.03. Found: C, 27.42; H, 2.62; I, 66.74.

EXAMPLE 19

(E,E)-1-(2,4,6-Triiodophenoxy)-3,7,11-trimethyl-2,6,10-dodecatriene

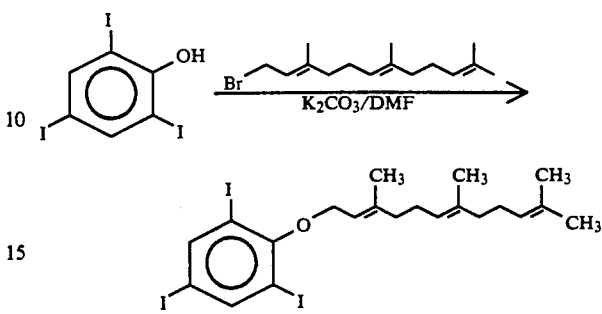

A mixture of triiodophenol (17.3 g, 36.8 mmol), farnesyl bromide (10 g, 35 mmol) and potassium carbonate (5.0 g, 36.2 mmol, 1.05 eq) in 40 ml of N,N-dimethylformamide was heated at 80°-100° C. for 3 hrs. The mixture was cooled and poured into water whereupon an oil precipitated after briefly stirring rapidly. The bulk of the water was decanted and the residue was take up in dichloromethane. The organic layer was washed with water, dried over magnesium sulfate and filtered through a pad of silica gel. The combined filtrate was concentrated under vacuum leaving the crude farnesyl ether derivative which was purified by silica gel chromatography (hexanes/ethyl acetate 9:1) to give the desired product as an oil in 41% yield. Title Compound: $^1$H (300 MHz) and $^{13}$C (75 MHz) NMR spectra were consistent with the desired structure. Calculated for $C_{21}H_{27}I_3O$: C, 37.36; H, 3.88; I, 56.39. Found: C, 37.68; H, 3.95; I, 55.97.

EXAMPLE 20

1-(2,4,6-Triiodophenoxy)-3,7-dimethyl-6-octene

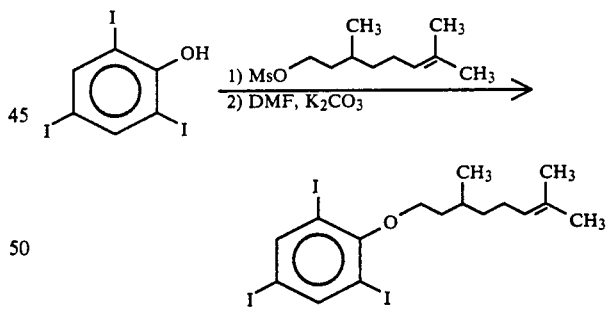

To a stirred solution of citronellol (4.5 g, 28.8 mmol) and triethylamine (5.2 ml, 34.6 mmol, 1.2 eq) in dichloromethane (50 ml) cooled to 0° C. was added dropwise, a solution of methanesulfonyl chloride (2.46 ml, 28.8 mmol) in dichloromethane (50 ml). The solution was stirred for 1 hr. at 0° C. under nitrogen and then water was added. The dichloromethane layer was dried over magnesium sulfate after washing with saturated aqueous sodium chloride and then concentrated in vacuo to give an oil. $^1$H-NMR (300 MHZ) spectrum of the oil indicated the desired methanesulfonate ester. The methanesulfonate ester was added to a stirred mixture of 2,4,6-triiodophenol (13.6 g, 28.8 mmol) and potassium carbonate (4.0 g, 28.8 mmol) in dimethylformamide (50 ml). The mixture was heated to 100° C. for 30 minutes and cooled to room temperature. The crude product was isolated by partitioning the reaction mixture between water and dichloromethane. The organic layer was concentrated under vacuum to give an oil. The oil was purified by flashing through basic alumina with hexanes to give the desired product in 15% yield as a light-sensitive oil. Title Compound: $^1$H (300 MHz) and $^{13}$C (75 MHz) NMR spectra were consistent with the desired structure. Calculated for $C_{16}H_{21}I_3O$: C, 31.50; H, 3.47; I, 62.41. Found: C, 31.71; H, 3.41; I, 62.30.

EXAMPLE 21

(E)-1-(3,5-Dimethyl-2,4,6-triiodophenoxy)-3,7-dimethyl-2,6-octadiene

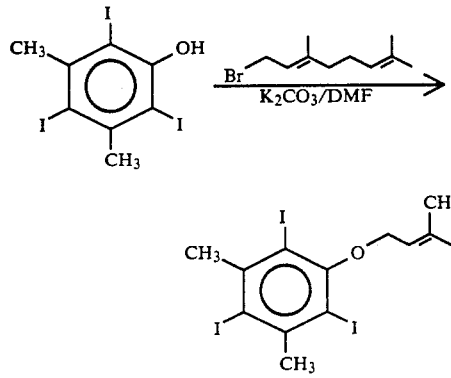

Using the procedure described for the synthesis of (E)-(2,4,6-triiodophenoxy)-3,7-dimethyl-2,6-octadiene, (E)-1-(3,5-dimethyl-2,4,6-triiodophenoxy)-3,7-dimethyl-2,6-octadiene was prepared in 37% yield from 3,5-dimethyl-2,4,6-triiodophenol (2.0 g, 4.0 mmol), geranyl bromide (0.87 g, 4.0 mmol) and potassium carbonate (0.55 g, 4.0 mmol) in 20 ml of dimethylformamide. Recrystallization from hexanes afforded analytically pure product. Mp 65°-66° C. Title Compound: $^1$H (300 MHz) and $^{13}$C (75 MHz) NMR spectra were consistent with the desired structure. Calculated for $C_{18}H_{23}I_3O$: C, 33.99; H, 3.64; I, 59.85. Found: C, 34.15; H, 3.58; I, 59.84.

EXAMPLE 22

(E)-1-(2,4,6-triiodophenoxy)-3,7-dimethyl-2,6-octadiene

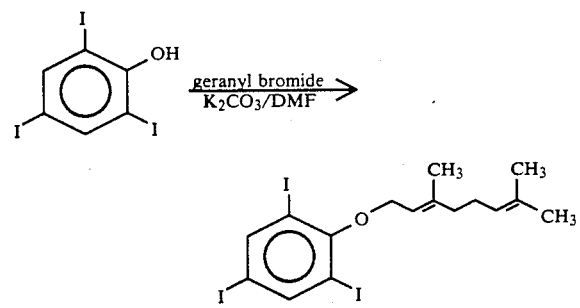

A mixture of triiodophenol (10.0 g, 21.2 mmol), milled potassium carbonate (3.1 g, 22.5 mmol, 1.06 eq) and geranyl bromide (4.0 ml, 20.2 mmol) in dimethyl formamide (25 ml) was heated to 50° C. for 2 hrs and cooled. The mixture was poured into 300 ml of water and extracted with ethyl acetate. The ethyl acetate extract was filtered through a short pad of silica gel, then alumina, eluting with ethyl acetate-hexanes (1:1). The eluent was concentrated under high vacuum to give the product in 87% yield as an oil. Title Compound: $^1$H (300 MHz) and $^{13}$C (75 MHz) NMR spectra were consistent with the desired structure. Calculated for $C_{16}H_{19}I_3O$: C, 31.61; H, 3.15; I, 62.61. Found: C, 31.84; H, 3.06; I, 62.60.

EXAMPLE 23

1-(2,4,6-Triiodophenoxy)-3-octyne

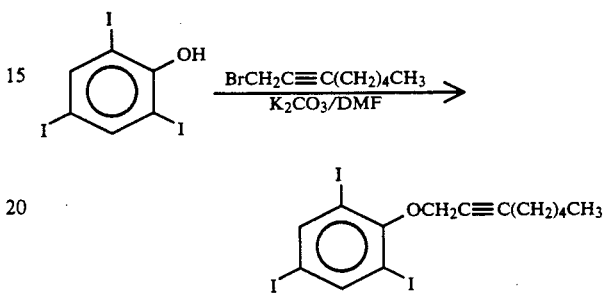

A mixture of triiodophenol (1.0 g, 2.1 mmol) and potassium carbonate (0.35 g, 2.54 mmol, 1.2 eq) in 4 ml of dimethylformamide was heated at 70° C. for 1 hr and then cooled to room temperature. 1-bromo-3-octyne was added in a single portion and the mixture was stirred for 1 hr. The reaction mixture was poured into water and the precipitated solids were collected by filtration. The collected solid was recrystallized from methanol to give 0.39 g (32%) of desired product. Mp 45° C.–49° C. Title Compound: $^1$H (300 MHz) and $^{13}$C (75 MHz) NMR spectra were consistent with the desired structure. Calculated for $C_{14}H_{15}I_3O$: C, 28.99; H, 2.61; I, 65.64. Found: C, 28.92; H, 2.49; I, 65.67.

EXAMPLE 24

2-(2,4,6-Triiodophenoxy)-4-octyne

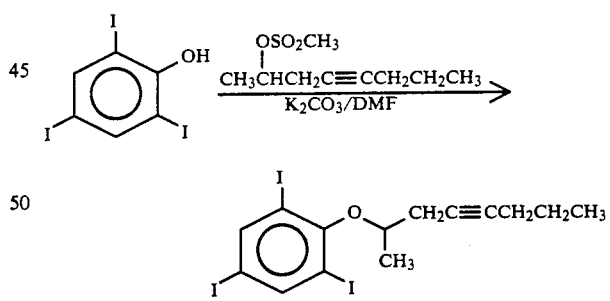

To a cooled solution of 4-octyn-2-ol (5.0 g, 39.6 mmol) in pyridine (40 ml) at −10° C. (ice/salt) was added dropwise methanesulfonyl chloride (4.6 ml, 59.4 mmol, 1.5 eq.) and the solution was stirred for 2.5 hrs. The reaction mixture was poured into water (25 ml) and extracted with dichloromethane. The organic layer was washed with 2N aqueous hydrochloric acid, saturated aqueous sodium bicarbonate and dried over magnesium sulfate. The organic layer was filtered and evaporated to give an oil (8.48 g, quantitative yield) which was stored in the freezer and used without further purification. $^1$H-NMR (300 MHZ) spectral data was consistent with the desired methanesulfonate ester.

A mixture of 2,4,6-triiodophenol (10.9 g, 23.1 mmol) and potassium carbonate (3.51 g, 25.4 mmol) in dimethylformamide (45 ml) was heated at 70° C. for 2.5 hrs and a solution of (4-octyn-2-yl)-methanesulfonate (6.12 g, 30.0 mmol, 1.3 eq.) in a minimum amount of dimethylformamide was added. The mixture was then heated to 110° C. overnight. After cooling the reaction mixture was poured into water and extracted with ethyl acetate. The organic layer was washed with water several times and dried over magnesium sulfate, filtered and concentrated to an oil. Silica gel chromatography (1% ethyl acetate-hexanes) gave 6.48 g, (48%) of the product as a yellow-orange oil. Additional filtration through silica gel gave colorless material. Title Compound: $^1$H (300 MHz) and $^{13}$C (75 MHz) NMR spectra were consistent with the desired structure. Calculated for $C_{14}H_{15}I_3O$: C, 28.99; H, 2.61; I, 65.64. Found: C, 29.23; H, 2.53; I, 65.45.

EXAMPLE 25

1-(2,4,6-Triiodophenoxy)-3-octyne

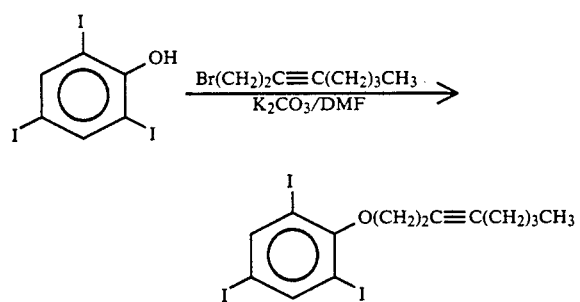

Triphenylphosphonium dibromide (36.8 g, 87.2 mmol) was suspended in diethyl ether at −20° C. and a solution of 3-octyne-1-ol (10.0 g, 79.2 mmol) was added dropwise over a twenty minute period. The mixture was allowed to stir overnight. The mixture was poured into ice-water and solids precipitated which were collected by filtration. The organic layer was separated, washed with 1N aqueous sodium hydroxide, water and dried over magnesium sulfate. The organic layer was then filtered and concentrated in vacuo to give a residue which was taken up in hexanes, filtered to remove undissolved material and concentrated to give 1-bromo-3-octyne as an orange oil (14.2 g, 96%). $^1$H NMR (300 MHZ) spectral data were consistent with the desired bromide (plus a trace of triphenylphosphine), and the crude product was used directly in the next step.

A mixture of 2,4,6-triiodophenol (1.0 g, 21 mmol) and potassium carbonate (351 mg, 2.54 mmol) in dimethylformamide (4 ml) was heated at 60° C. for 1 hour and then 1-bromo-3-octyne (0.4 g, 2.1 mmol) was added. After heating for an additional hour the mixture was stirred at room temperature for 72 hours. The reaction was poured into water and the precipitated solids were collected to give the crude product. The crude product was recrystallized from methanol to give 0.24 g (50%) of the octynyl ether, mp 79°–81° C. Title Compound: $^1$H (300 MHz) and $^{13}$C (75 MHz) NMR spectra were consistent with the desired structure. Calculated for $C_{14}H_{15}I_3O$: C, 28.99; H, 2.61; I, 65.64. Found: C, 29.05; H, 2.53; I, 65.92.

EXAMPLE 26

Diethyl 2-(2,4,6-Triiodophenoxy)-1,3-propanedioate

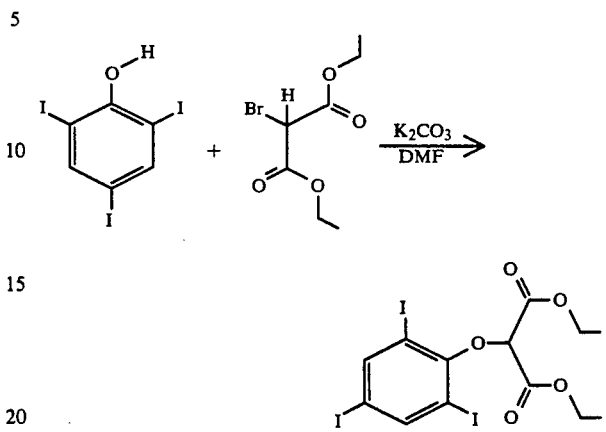

A stirred mixture of 70.8 g (0.15 mol) of 2,4,6-triiodophenol, 39.0 g (0.15 mol) of diethyl bromomalonate and 20.7 g (0.15 mol) of milled anhydrous potassium carbonate in 200 ml of dry dimethylformamide was heated at 100° C. under argon for 5 hours. The mixture was cooled and concentrated in vacuo. The resulting residue was combined with 300 ml of ice-cold water and the oily product was extracted with ethyl acetate (1×300 ml), 3×100 ml). The combined ethyl acetate extracts were dried (MgSO$_4$) and concentrated in vacuo to a dark oil. The oil was purified by chromatography (eluted by hexanes to 20% diethyl ether in hexanes) to yield 60.2 g (64%) of product as a light cream-colored solid. Title Compound: $^1$H (300 MHz) and $^{13}$C (75 MHz) NMR spectra were consistent with the desired structure. FAB/MS: M+ 631; Calculated for $C_{13}H_{13}I_3O_5$: C, 24.79; H, 2.08; I, 60.44. Found: C, 25.07; H, 2.00; I, 60.09.

EXAMPLE 27

Diisopropyl 2-(2,4,6-Triiodophenoxy)-1,3-propanedioate

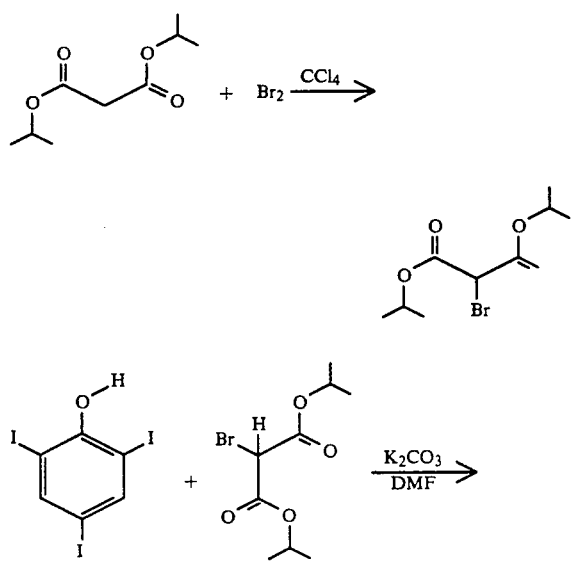

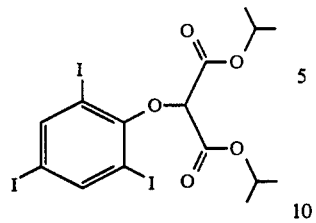

A stirred solution of 18.8 g (0.1 mol) of diisopropyl malonate in 100 ml carbon tetrachloride was cooled in an ice bath and 15.8 g (0.1 mol) bromine was added dropwise over a 90 minute period. The ice bath was removed and the reaction stirred at room temperature for 20 hours. The reaction solution was concentrated in vacuo and the resulting residue distilled to yield 16.1 g (76%) of the bromomalonate I [H. P. Gallus and A. K. Macbeth, *J. Chem. Soc.*, 1937, 1810–12] as a clear colorless liquid; Bp 51°-2° C./0.1 mm Hg. CI/MS: MH+ 267. $^1$H-NMR (300 MHZ) spectral data was consistent with the desired structure. Using the same procedure as for 2-(2,4,6-triiodophenoxy)-1,3-propanedioic acid, diethyl ester, but substituting methylene chloride for ethyl acetate in the aqueous extraction, 2-(2,4,6-triiodophenoxy)-1,3-propanedioic acid, diisopropyl ester was prepared from 8.6 g (0.03 mol) of malonate I, 107 g (0.03 mol) of 2,4,6-triiodophenol, 4.5 g (0.03 mol) of milled anhydrous potassium carbonate and 30 ml of dimethylformamide in 69% yield as a tan oil; bp>65° C./0.65 mm Hg after chromatography (hexanes to 5% ether in hexanes). Title Compound: $^1$H (300 MHz) and $^{13}$C (75 MHz) NMR spectra were consistent with the desired structure. FAB/MS: MH+ 659. Calculated for $C_{15}H_{17}I_3O_5$: C, 27.38 H, 2.60; I, 57.86. Found: C, 27.45; H, 2.56; I, 57.82.

EXAMPLE 28
Ethyl 2,2-Bis-(3-iodophenoxy)acetate

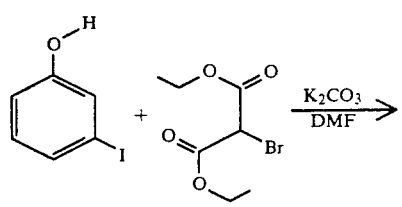

A stirred solution of 40.0 g (0.18 mol) of 3-iodophenol, 33.6 ml (0.18 mol) of diethyl bromomalonate and 27.63 g (0.2 moles) of milled anhydrous potassium carbonate in 250 ml dry N,N-dimethylformamide was heated at 110°-120° C. under argon for 14 hours. The mixture was cooled and concentrated in vacuo. The resulting residue was combined with 600 ml of ice-cold water and the oily product was extracted with ethyl acetate (4×150 ml). The combined ethyl acetate extracts were dried (MgSO$_4$) and concentrated in vacuo to an orange oil. The orange oil was purified by chromatography (eluted by 5% methylene chloride in hexanes to 50% methylene chloride in hexanes) to yield 8.1 g (8.5%) of the desired product as a tan oil. Title Compound: $^1$H (300 MHz) and $^{13}$C (75 MHz) NMR spectra were consistent with the desired structure. FAB/MS: M+ 524. Calculated for $C_{16}H_{14}I_2O_4$: C, 36.67 H, 2.69; I, 48.43. Found: C, 36.92; H, 2.65; I, 48.24.

EXAMPLE 29
Ethyl 5-(2,4,6-triiodophenoxy)hexanoate

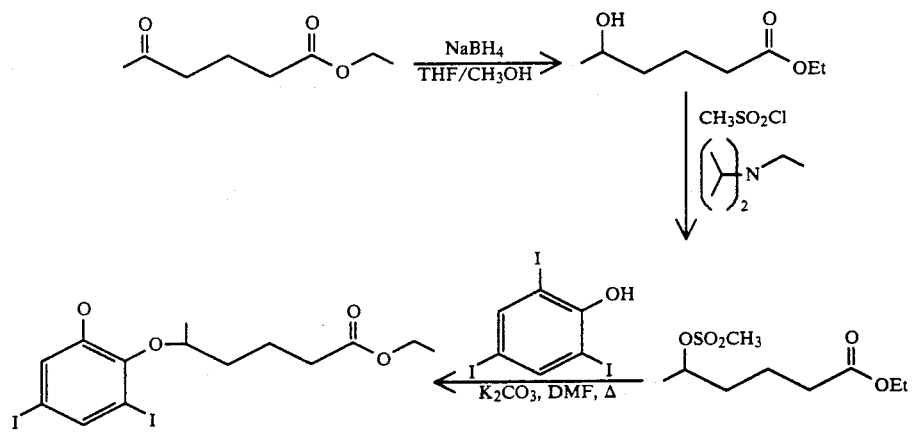

To a solution of ethyl 5-oxo-hexanoate (23.8 g, 150 mmol) in THF (270 ml) was added methanol (30 ml). The reaction flask was immersed in an ice/water bath and sodium borohydride (2.3 g, 60.8 mmol) was added. The reaction was stirred for 16 hrs with warming. At this point more sodium borohydride (2.3 g, 60.8 mmol) was added to the reaction flask. After a period of 2 hrs, the reaction was poured into a stirred mixture of crushed ice (250 g), saturated aqueous ammonium hydroxide (250 ml) and ether (500 ml). After stirring for 2 hrs, the organic phase was separated. The aqueous phase was extracted with EtOAc (2×200 ml). The organic washings were dried (Na$_2$SO$_4$), filtered an evaporated in vacuo to provide a light yellow solid (22.2 g). The product was purified by flash column chromatography (silica, 1:4, ethylacetate:hexanes) to give ethyl 5-hydroxyhexanoate (20.3 g, 85%) as a white solid.

Ethyl 5-methanesulfonyloxy hexanoate was prepared as previously described from ethyl-5-hydroxy-hexanoate (20.9 g, 130 mmol), mesyl chloride (14.0 ml, 180 mmol) and diisopropylethylamine (27.2 ml, 157 mmol) in 95% yield.

Ethyl 5-5-methanesulfonyloxy (33.3 g, 124 mmol), 2,4,6-triiodophenol (58.5 g, 124 mmol) and potassium carbonate (17.1 g, 124 mmol) were reacted in DMF (242 ml) at 82° C. as described for 2-(4-iodophenoxy)decane. After stirring for 21 hrs, the reaction was processed as for 2-(4-iodophenoxy)decane except at five times the volumes to produce a viscous yellow oil (87.4 g). This product was further purified by flash column chromatography (silica, hexanes) to give ethyl-5-(2,4,6-triiodophenoxy)hexanoate (40.0 g, 50.0%) as a viscous oil. Title Compound: $^1$H (300 MHz) and NMR spectra were consistent with the desired structure. Calculated for $C_{14}H_{17}I_3O_3$: C, 27.39; H, 2.79; I, 62.01. Found: C, 27.65, H, 2.72; I, 62.21.

EXAMPLE 30

5-(2,4,6-Triiodophenoxy)-hexan-1-ol

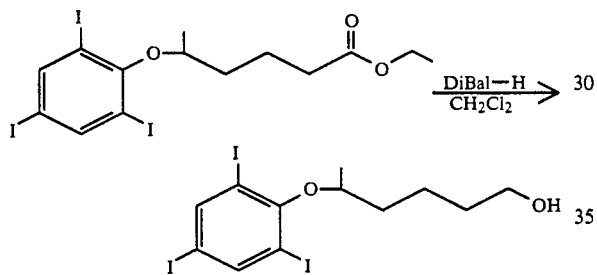

A flask containing ethyl 5-(2,4,6-triiodophenoxy)hexanoate (16.3 g, 26.5 mmol) was charged with dry dichloromethane (133 ml). The reaction flask was fitted with an addition funnel, put under an atmosphere of $N_2$ and placed in a dry ice/acetone bath. The addition funnel was charged with a solution of DiBAl-H in hexanes (1.0M, 58.5 ml, 58.5 mmol) which was added to the stirred reaction mixture over a period of 0.5 h. After stirring at −78° C. for 2.5 hrs, the addition funnel was charged with DiBAl-H solution (20 ml, 20 mmol) which was added to the reaction over a period of 0.25 hr. After stirring for 1 hr, the dry ice/acetone bath was replaced with an ice/water bath. After 1 hr, the dry ice/acetone bath was replaced and the reaction was quenched by the slow addition of $CH_3OH$ (5 ml). The reaction mixture was poured into a stirred mixture of EtOAc (600 ml and saturated aqueous Rochelle's salt (400 ml). After vigorously stirring for 3 hrs, the layers were separated. The organic phase was washed with saturated aqueous Rochelle's salt (250 ml) and brine (250 ml), dried ($Na_2SO_4$) and evaporated in vacuo to give a light yellow residue (13.2 g). Recrystallization from EtOAc/hexanes provided 5-(2,4,6-triiodophenoxy)-hexan-1-ol (12.6 g, 83%) as a white solid. Mp 79°–80° C. (from ethylacetate/hexanes). Title Compound: $^1$H (300 MHz) and $^{13}$C (75 MHz) NMR spectra were consistent with the desired structure. Calculated for $C_{12}H_{15}I_3O_2$: C, 25.20; H, 2.64; I, 66.56. Found: C, 25.31, H, 2.58; I, 66.81.

EXAMPLE 31

10-(4-Iodophenoxy)-undecan-1-ol

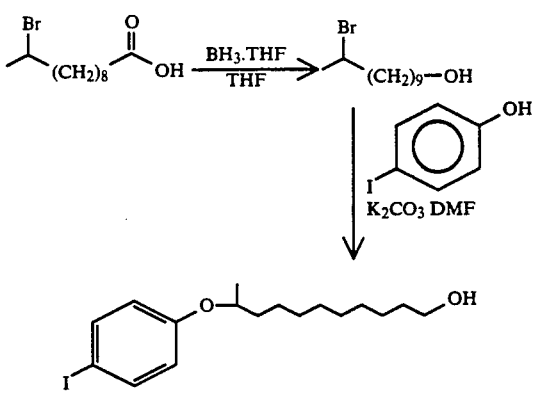

A. Preparation of 10-bromoundecan-1-ol

A flask containing 10-bromoundecanoic acid (25.0 g, 94.2 mmol) was charged with dry THF (250 ml), immersed in an ice/water bath and fitted with an addition funnel. The addition funnel was charged with borane-THF solution (1.0M, 113 ml, 113 mmol) which was added to the stirred reaction mixture over a period of 45 minutes. 3 hrs after the addition was completed, the reaction was poured into a stirred mixture of EtOAc (500 ml) and 10% aqueous potassium carbonate (300 ml). After vigorously stirring for 0.5 hr, the layers were separated. The organic phase was washed with water (250 ml) and brine (250 ml), dried ($Na_2SO_4$), filtered and evaporated in vacuo. Flash column chromatography (silica, 1:4; EtOAc:hexanes) provided 10-bromo-undecan-1-ol (20.8 g, 88%).

B. Preparation of 10-(4-iodophenoxy)-undecan-1-ol

A reaction flask was charged with dry DMF (150 ml), 4-iodophenol (26.3 g, 119 mmol) and potassium carbonate (16.5 g, 119 mmol), immersed in an oil bath and heated to 75° C. over a period of 0.5 hr. After stirring at 75° C. for 0.5 hr, the reaction was fitted with an addition funnel which was charged with 10-bromoundecan-1-ol (20.0 g, 79.6 mmol) in a solution of dry DMF (100 ml). The solution was added to the reaction mixture over a period of 14 hrs. The oil bath temperature was then increased to 90° C. After stirring for an additional 24 hrs, the reaction was allowed to cool, diluted with DMF, filtered through a pad of celite and evaporated in vacuo. The resulting residue was taken up into EtOAc (750 ml), washed with brine (300 ml), water (300 ml), 1M aqueous sodium hydroxide (300 ml), water (300 ml) and brine (300 ml), dried ($Na_2SO_4$), filtered and evaporated to provide a light brown residue (33.1 g). The product was purified by repeated flash column chromatography (3×, silica, 1:9-1:4; EtOAc:hexanes) to provide 10-(4-iodophenoxy)-undecan-1-ol (12.1 g, 39%) as a light yellow oil. Title Compound: $^1$H (300 MHz) and $^{13}$C (75 MHz) NMR spectra were consistent with the desired structure. Calculated for $C_{17}H_{27}IO_2$: C, 52.31; H, 6.97; I, 32.50. Found: C, 52.00, H, 6.93; I, 32.71.

EXAMPLE 32

Ethyl 5-(2,4,6-triiodophenoxy) hexyl carbonate

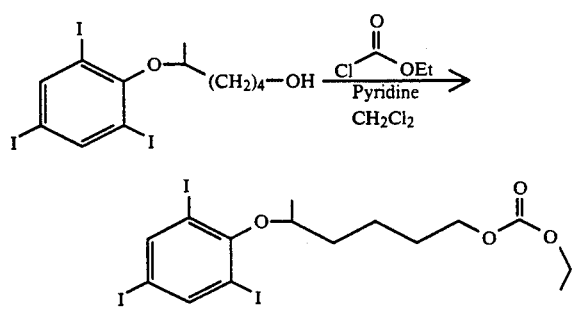

A flask containing 5-(triiodophenoxy)-hexan-1-ol (6.0 g, 10.5 mmol) was charged with dry $CH_2Cl_2$ (50 ml) and dry prydine (9.6 ml, 105 mmol), placed under an atmosphere of $N_2$ and immersed in an ice/water bath. After 0.25 hr, ethyl chloroformate (8.1 ml, 105 mmol) was added over a period of 0.25 hrs via syringe. The reaction was allowed to stir with slow warming. After stirring for 4 hrs, the reaction was diluted with ether (250 ml), washed with water (100 ml), 1M aqueous HCl (2×100 ml), water (2×100 ml) and brine (100 ml), dried ($Na_2SO_4$), filtered and evaporated in vacuo. Flash column chromatography (silica, 1:9; EtOAc: hexanes) provided the product (6.49 g, 96%) as a light yellow oil. Title Compound: $^1H$ (300 MHz) and $^{13}C$ (75 MHz) NMR spectra were consistent with the desired structure. Calculated for $C_{15}H_{19}I_3O_4$: C, 27.97; H, 2.97; I, 59.11. Found: C, 28.06, H, 2.92; I, 58.92.

EXAMPLE 33

Ethyl 10-(3-iodophenoxy)-undecanoate

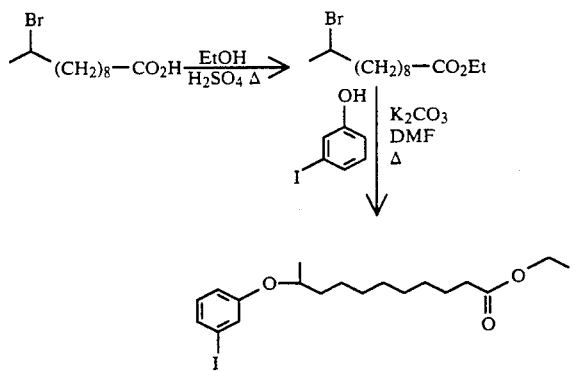

A. Preparation of ethyl 10-bromoundecanoate

10-Bromoundecanoic acid (10.0 g, 87.7 mmol) obtained according to Rolla, F. and Landini, D., *J. Org. Chem.*, 1980, 45, 3527-3529; Ashtor, R. and Smith, J. C., *J. Chem. Soc.*, 1934, 435-440, was added to a stirred solution of concentrated sulfuric acid (4 ml) in ethanol (155 ml). The reaction flask was fitted with a reflux condenser and immersed in an oil bath which was brought to 120° C. over a 0.5 hr period. After refluxing for 3 hrs, the reaction was allowed to cool and poured into ether (500 ml). The ether was washed with saturated aqueous sodium bicarbonate (5×150 ml) and brine (2×150 ml), dried ($Na_2SO_4$), filtered and evaporated in vacuo. Flash column chromatography (silica, 2.5% EtOAc in hexanes) provided ethyl 10-bromoundecanoate as a low melting solid.

B. Preparation of ethyl 10-(3-iodophenoxy)-undecanoate

To a stirred solution of ethyl 10-bromoundecanoate (9.7 g, 33.0 mmol) in dry DMF (66 ml) was added 3-iodophenol (7.99 g, 36.3 mmol) and potassium carbonate (5.02 g, 37.6 mmol). The reaction was immersed in an oil bath which was warmed to 75° C. over 0.5 hr. After stirring for 14 hrs under an $N_2$ atmosphere, the oil bath temperature was increased to 85° C. After stirring for an additional 4 hrs at 85° C., the reaction was allowed to cool, diluted with DMF (200 ml), filtered through a pad of celite and evaporated in vacuo. The resulting residue was taken up in ether (500 ml). The organic phase was washed with water (100 ml), 1M aqueous sodium hydroxide (100 ml), water (2×100 ml) and brine (100 ml), dried ($Na_2SO_4$), filtered and evaporated in vacuo to provide crude ethyl 10-(3-iodophenoxy)-undecanoate which was contaminated with olefinic esters. Flash column chromatography (silica, 1-2% ; EtOAc in hexanes) provide ethyl 10-(3-iodophenoxy)-undecanoate as a clear oil (4.75 g, 33.3%). Title Compound: $^1H$ (300 MHz) and $^{13}C$ (75 MHz) NMR spectra were consistent with the desired structure. FAB/MS: M+432. Calculated for $C_{19}H_{29}IO$: C, 52.78; H, 6.77; I, 29.35. Found: C, 52.74, H, 6.77; I, 29.26.

Compositions of the Present Invention

The contrast agents may be formulated for administration using physiologically acceptable carriers or excipients in a manner within the skill of the art. The compounds with the addition of pharmaceutically acceptable aids (such as surfactants and emulsifiers) and excipients may be suspended or partially dissolved in an aqueous medium resulting in a dispersion, solution or suspension. However, the oily contrast agents are preferably made into emulsions.

Compositions of the present invention comprise the following pharmaceutically acceptable components based on % w/v:

| | |
|---|---|
| Non-aqueous phase | 1–50 |
| Polymeric Material | 0.001–15 |
| Divalent Cation | 0.001–15 |
| Contrast Agent | 0.001–75 |
| Excipient | 0–20 |
| Aids/Surfactants/Emulsifiers | 0.01–15 |
| Water | q.s. to 100 |

Specific Examples of the compositions of the present invention are shown in Examples 34–36.

| Example No. 34 | |
|---|---|
| 2,4,6-Triiodophenoxymethylcyclopentane | 23.7% (w/v) |
| Safflower Oil | 20.0% (w/v) |
| Kappa Carrageenan | 2.0% (w/v) |
| Calcium Lactate | 2.0% (w/v) |
| Tween 21 | 2.5% (w/v) |
| Hydroxypropylmethylcellulose (4000 cPs) | 0.5% (w/v) |
| q.s. with water to 100% volume and shake | |

| Example No. 35 | |
|---|---|
| 2-(4-Iodophenoxy)pentadecane | 55.3% (w/v) |
| Dow Corning Medical Antifoam AF | 40.0% (w/v) |

-continued

| Example No. 35 | |
|---|---|
| Pectin | 4.0% (w/v) |
| Calcium Lactate | 2.0% (w/v) |
| q.s. with water to 100% volume and shake | |

| Example No. 36 | |
|---|---|
| 2-Iodophenoxycyclopentane | 25.9% (w/v) |
| Simplesse ® Dietary Fat Substitute | 30.0% (w/v) |
| Heparin | 1.0% (w/v) |
| Magnesium Carbonate | 1.0% (w/v) |
| Hydroxypropylmethylcellulose (4000 cPs) | 0.5% (w/v) |
| q.s. with water to 100% volume and shake | |

The nonaqueous phase comprises vegetable oils such as safflower oil; non-metabolizing fat substituents, such as Simplesse; fluorinated hydrocarbons, such as perfluorodecalin; mineral oil and simethicone.

Excipients advantageously used in the formulations include viscosity mediating and stabilizing agents, such as microcrystalline cellulose, ethylcellulose, hydroxypropyl methylcellulose and gum arabic. Physiologically acceptable substances may also be included, such as sodium citrate, sodium chloride, therapeutic substances, antacid substances and flavoring agents. The inclusion of antimicrobial/antiseptic agents such as methyl parahydroxybenzoate, ethyl parahydroxybenzoate, propyl parahydroxybenzoate, benzoic acid or sorbic acid may also be desirable in some formulations.

As known by those skilled in the art, surfactants or emulsifiers can reduce the interfacial tension between two immiscible phases, i.e., oil-in-aqueous medium. These agents can be used alone or in combination with other emulsifying agents and surfactants. For example, Dow Corning Medical Antifoam AF, which is a composition of 30% w/v polydimethylsiloxane simethicone and silica aerogel, 14% w/v stearate emulsifiers and 0.075% w/v sorbic acid, the balance being water, may be used by itself. Intralipid, which is an emulsion of fatty acids needs the presence of a suspending agent for it to form an acceptable emulsion with contrast agents of the present invention. The amount of such surfactants may be in the range of from 0.01 to 15% w/v of the aqueous formulations, although the amount, in general, is kept as low as possible, preferably in the range of 0.05 to 5% w/v. The surface active agents may be cationic, anionic, nonionic, zwitterionic or a mixture of two or more of these agents.

Suitable cationic surfactants include cetyl trimethyl ammonium bromide. Suitable anionic agents include sodium lauryl sulphate, sodium heptadecyl sulphate, alkyl benzenesulphonic acids and salts thereof, sodium butylnapthalene sulfonate, and sulphosuccinates. Zwitterionic surface active agents are substances that when dissolved in water they behave as diprotic acids and, as they ionize, they behave both as a weak base and a weak acid. Since the two charges on the molecule balance each other out the molecules act as neutral molecules. The pH at which the zwitterion concentration is maximum is known as the isoelectric point. Compounds, such as certain amino acids having an isoelectric point at the desired pH of the formulations of the present invention are useful in practicing the present invention.

In preparing the formulations of the present invention we prefer to use nonionic emulsifiers or surface active agents which, similarly to the nonionic contrast agents, possess a superior toxicological profile to that of anionic, cationic or zwitterionic agents. In the nonionic emulsifying agents the proportions of hydrophilic and hydrophobic groups are about evenly balanced. They differ from anionic and cationic surfactants by the absence of charge on the molecule and, for that reason, are generally less of an irritant than the cationic or anionic surfactants. Nonionic surfactants include carboxylic esters, carboxylic amides, ethoxylated alkylphenols and ethoxylated aliphatic alcohols.

One particular type of carboxylic ester nonionic surface active agents are the partial, for example mono-, esters formed by the reaction of fatty and resin acids, for example of about 8 to about 18 carbon atoms, with polyhydric alcohols, for example glycerol, glycols such as mono-, di-, tetra- and hexaethylene glycol, sorbitan, and the like; and similar compounds formed by the direct addition of varying molar ratios of ethylene oxide to the hydroxy group of fatty acids.

Another type of carboxylic esters is the condensation products of fatty and resin partial acids, for example mono-, esters ethylene oxide, such as fatty or resin acid esters of polyoxyethylene sorbitan and sorbitol, for example polyoxyethylene sorbitan, monotall oil esters. These may contain, for example, from about 3 to about 80 oxyethylene units per molecule and fatty or resin acid groups of from about 8 to about 18 carbon atoms. Examples of naturally occurring fatty acid mixtures which may be used are those from coconut oil and tallow while examples of single fatty acids are dodecanoic acid and oleic acid.

Carboxylic amide nonionic surface active agents are the ammonia, monoethylamins and diethylamine amides of fatty acids having an acyl chain of from about 8 to about 18 carbon atoms.

The ethoxylated alkylphenol nonionic surface active agents include various polyethylene oxide condensates of alkylphenols, especially the condensation products of monoalkylphenols or dialkylphenols wherein the alkyl group contains about 6 to about 12 carbon atoms in either branched chain or particularly straight chain configuration, for example, octyl cresol, octyl phenol or nonyl phenol, with ethylene oxide, said ethylene oxide being present in amounts equal to from about 5 to about 25 moles of ethylene oxide per mole of alkylphenol.

Ethoxylated aliphatic alcohol nonionic surface active agents include the condensation products of aliphatic alcohols having from about 8 to 18 carbon atoms in either straight chain or branched chain configuration, for example oleyl or cetyl alcohol, with ethylene oxide, said ethylene oxide being present in equal amounts from about 30 to about 60 moles of ethylene oxide per mole of alcohol.

Preferred nonionic surface active agents include: sorbitan esters (sold under the trade name Span) having the formula:

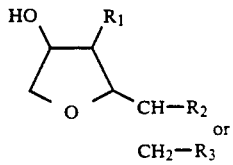

or
$CH_2-R_3$ wherein
$R_1=R_2=OH$, $R_3=R$ for sorbitan monoesters,
$R_1=OH$, $R_2=R_3=R$ for sorbitan diesters, $R_1=R_2=R_3=R$ for sorbitan triesters,
where $R=$
(C$_{11}$H$_{23}$) COO for laurate,
(C$_{17}$H$_{33}$) COO for oleate,
(C$_{15}$H$_{31}$) COO for palmitate,
(C$_{17}$H$_{35}$) COO for stearate.

Polyoxyethylene alkyl ethers (i.e. Brijs) having the formula:

$$CH_3(CH_2)_x(O-CH_2-CH_2)_yOH$$

where (x+1) is the number of carbon atoms in the alkyl chain, typically:
12 lauryl (dodecyl)
14 myristyl (tetradecyl)
16 cetyl (hexadecyl)
18 stearyl (octadecyl)
and y is the number of ethylene oxide groups in the hydrophilic chain, typically 10-60.

Polyethylene sorbitan fatty acid esters, sold under the trade names of Polysorbates 20, 40, 60, 65, 80 & 85.

Polyethylene stearates, such as:
poly(oxy-1,2-ethanediyl),α-hydro-ω-hydroxyoctadecanoate;
polyethylene glycol monostearate; and
poly(oxy-1,2-ethanediyl)-α-(1-oxooctadecyl)-ω-hydroxypolyethylene glycol monostearate The film former polymeric materials used in accordance with the present invention include anionic polymers, cationic polymers and neutral polymers.

I. Anionic Polymers

The anionic polymers carry negative charges in the ionized form and are capable of binding to cell surface mainly by electrostatic forces. Suitable anionic polymers include the following:

$$R-O-\underset{\underset{O}{\parallel}}{\overset{\overset{O}{\parallel}}{S}}-O-M^{++}, \quad R-\overset{\overset{O}{\parallel}}{C}-O-M^{++},$$

$$R-O-R-\overset{\overset{O}{\parallel}}{C}-O-M^{++}$$

wherein
R is the polymeric chain;

$$-O-\underset{\underset{O}{\parallel}}{\overset{\overset{O}{\parallel}}{S}}-O- \quad \text{and} \quad \overset{\overset{O}{\parallel}}{C}-O-$$

are anionic ligands; and
M$^{++}$ is a divalent cation.

Specific anionic polymers useful in the practice of the present invention include:

(1) Sulfated polysaccharides of the formula:

$$R-O-\underset{\underset{O}{\parallel}}{\overset{\overset{O}{\parallel}}{S}}-O-M^{++}$$

wherein
R is
3,6-anhydro-D-galactose linked through C-4 to D-galactose; (kappa carrageenan)
α-D-galactose units (1-3) linked; (lambda carrageenan)
D-galactose 3,6-anhydro-D-galactose; (iota carrageenan)
D-galactose 3,6-anhydro-L-galactose: (Agar-Agar)
D-galactose 3,6-anhydro-D-galactose; (Furcellaren)
D-glucopyranose; (Laminarin sulfate)
Galactan; and (Galactan sulfate)
Galactosamino-glucuronans (Chondroitin sulfates); and
M$^{++}$ is Mg$^{++}$, Ca$^{++}$, Zn$^{++}$, Ba$^{++}$ or mixtures thereof.

(2) Carboxylated polysaccharides of the formula:

$$R-\overset{\overset{O}{\parallel}}{C}-O-M^{++}$$

wherein
R is
D-galacturonoglycan; and (Pectin)
anhydro-D-mannuronic acid and anhydro-L-guluronic acid (Algin) residues; and
M$^{++}$ is Mg$^{++}$, Ca$^{++}$, Zn$^{++}$, Ba$^{++}$ or mixtures thereof.

(3) Cellulose derivatives of the formulae:

$$R'-O-R-O-\underset{\underset{O}{\parallel}}{\overset{\overset{O}{\parallel}}{S}}-O-M^{++},$$

$$R'-O-\overset{\overset{O}{\parallel}}{C}-R-O-\underset{\underset{O}{\parallel}}{\overset{\overset{O}{\parallel}}{S}}-O-M^{++}$$

and $$R''-\overset{\overset{O}{\parallel}}{C}-R-\overset{\overset{O}{\parallel}}{C}-O-M^{++}$$

wherein
R is an anhydroglucose residue;
R' is CH$_3$, C$_2$H$_5$ or C$_3$H$_7$;
R'' is CH$_3$ or C$_2$H$_5$; and
M$^{++}$ is Mg$^{++}$, Ca$^{++}$, Zn$^{++}$, Ba$^{++}$ or mixtures thereof.

Examples of cellulose derivatives include: sodium ethylcellulose sulfate, sodium cellulose acetate sulfate and sodium carboxymethyl cellulose.

(4) Sulfated, sulfonated or carboxylated synthetic polymers of the formula:

$$R-\underset{\underset{O}{\parallel}}{\overset{\overset{O}{\parallel}}{S}}-O-M^{++}, \quad R-O-\underset{\underset{O}{\parallel}}{\overset{\overset{O}{\parallel}}{S}}-O-M^{++} \quad \text{and}$$

$$R-\overset{\overset{O}{\parallel}}{C}-O-M^{++}$$

wherein
R is an aliphatic or aromatic hydrocarbon, such as polystyrene, poly(sulfon) resin or carboxylated (poly) vinyl; and
M$^{++}$ is Mg$^{++}$, Ca$^{++}$, Zn$^{++}$, Ba$^{++}$ or mixtures thereof.

II. Cationic Polymers

The cationic polymers carry positive charges in the ionized form. Suitable polymers for practicing the present invention include: dermatan sulfate, keratosulfate, hyaluronic acid, heparin and chitin.

III. Neutral Polymers

Neutral polymers having polarizable electrons such as oxygen, nitrogen, sulfur, fluoride, chloride, bromide and iodide are also suitable for practicing the present invention. In the presence of a cation, such as $Mg^{++}$, $Ca^{++}$, $Zn^{++}$ or $Ba^{++}$, the polymers are partially polarized thereby providing intermolecular interactions between the polymer and the intestinal wall. Examples of these polymers include:

(a) Polysaccharides, such as starch, glycogen, glucan, fructans, mannans, galactomannas, glucomannans, galactans, xylans, glycuranans, dextran and starch amylose;

(b) Cellulose derivatives, such as methylcellulose, hydroxyethylcellulose, ethylhydroxyethyl cellulose, hydroxypropyl methylcellulose and hydroxypropyl cellulose; and (c) Synthetic polymers, such as polyvinylpyrrolidone, polyvinyl alcohol and ethylene oxide polymers.

The dosages of the contrast agent used according to the method of the present invention will vary according to the precise nature of the contrast agent used. Preferably, however, the dosage should be kept as low as is consistent with achieving contrast enhanced imaging. By employing as small amount of contrast agent as possible, toxicity potential is minimized. For most contrast agents of the present invention dosages will be in the range of from about 0.1 to about 16.0 g iodine/kg body weight, preferably in the range of from about 0.5 to about 6.0 g iodine/kg of body weight, and most preferably, in the range of from about 1.2 to about 2.0 g iodine/kg body weight for regular X-ray visualization of the GI tract. For CT scanning, the contrast agents of the present invention will be in the range of from about 1 to about 600 mg iodine/kg body weight, preferably in the range of from about 20 to about 200 mg iodine/kg body weight, and most preferably in the range of from about 40 to about 80 mg iodine/kg body weight.

The concentration of the contrast agent should be in the range of from about 0.001% w/v to about 75% w/v of the formulation, preferably from about 0.05% w/v to about 50% w/v and most preferably of from about 0.1% w/v to about 20% w/v.

The concentration of the film forming polymeric material depends on the particular polymer used, however, it should be in the range of 0.001 to about 15% w/v or higher in combination with a divalent substance, such as calcium lactate, having a concentration range of 0.001 to 15% w/v. Dosage level of the polymeric material may be in the range of from about 2 to about 15 g/kg body weight or higher.

The compositions of the present invention possess very good adherence to the walls of the gastrointestinal tract by forming an essentially uniform coating thereon.

The invention having been fully described, it will be apparent to one skilled in the art that changes and modifications can be made thereto without departing from the spirit and scope thereof.

What is claimed is:

1. An x-ray contrast composition designed for depositing a thin, flexible film membrane onto the mucosal lining of the nutrient absorbing inner surface of the intestine of a patient to form a barrier between said nutrient absorbing inner surface and the content of said intestine, said flexible film membrane to remain bound to said mucosal lining until eliminated by normal cell turnover comprising based on w/w:

(a) of from about 0.001 to about 15% of a polymeric material capable of forming a film membrane on the gastrointestinal tract in the Ph range of from about 5 to about 8, said polymeric material is selected from the group consisting of anionic polymers carrying negative charges in the ionized form, cationic polymers carrying positive charges in the ionized form, and neutral polymers, said neutral polymers having polarizable electrons selected from the group consisting of oxygen, nitrogen, sulfur, fluoride, chloride, bromide and iodide: in combination with (b) of from about 0.001 to about 15% of a divalent cation to potentiate the binding of said flexible film membrane to said mucosal lining selected from the group consisting of $Ca^{++}$, $Mg^{++}$, $Zn^{++}$ and $Ba^{++}$; and (c) an x-ray contrast producing agent having the formula, or a pharmaceutically acceptable salt thereof

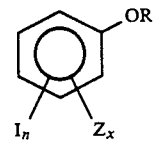

wherein

Z is H, halo, $C_1$–$C_{20}$ alkyl, cycloalkyl, lower alkoxy, cyano, where the alkyl and cycloalkyl groups can be substituted with halogen or halo-lower-alkyl groups;

R is $C_1$–$C_{25}$ alkyl, cycloalkyl, or halo-lower-alkyl, optionally substituted with halo, fluoro-lower-alkyl, aryl, lower-alkoxy, hydroxy, carboxy, lower-alkoxy carbonyl or lower-alkoxy-carbonyloxy, $(CR_1R_2)_p$—$(CR_3$=$CR_4)_mQ$, or $(CR_1R_2)_p$—C≡C—Q;

$R_1$, $R_2$, $R_3$ and $R_4$ are independently lower-alkyl, optionally substituted with halo;

x is 1–4;

n is 1–5;

m is 1–15;

p is 1–10; and

Q is H, lower-alkyl, lower-alkenyl, lower-alkynyl, lower-alkylene, aryl, or aryl-lower alkyl in a pharmaceutically acceptable carrier.

2. The composition according to claim 1 wherein said x-ray contrast agent is selected from the group consisting of: 2-(4-iodophenoxy)decane, 2-(2,4,6-triiodophenoxy)-pentadecane, 2-(2,4,6-triiodophenoxy)decane, (2,4,6-triiodophenoxy)-1H, 1H, 2H, 2H-perfluorooctane and 1-(2,4,6-triiodo-3-trifluorophenoxy)octane.

3. The composition according to claim 1 wherein said x-ray contrast agent is selected from the group consisting of: 2-(2,4,6-triiodophenoxy)-nonane, 2-ethyl-1-(2,4,6-triiodophenoxy)-hexane and 3,3-diphenyl-1-(2,4,6-triiodophenoxy)propane.

4. The composition according to claim 1 wherein said x-ray contrast agent is selected from the group consisting of: 3-(2,4,6-triiodophenoxy)-nonane, 2-(4-iodophenoxy)-undecane, 2-iodophenoxycyclopentane, 3-iodophenoxycyclopentane and (3,5-dimethyl-2,4,6-triiodophenoxy)cyclopentane.

5. The composition according to claim 1 wherein said x-ray contrast agent is selected from the group consisting of: 2-(4-iodophenoxy)pentadecane, 4-iodophenoxycyclopentane, 2,4,6-triiodophenoxycyclopentane, 2,4,6-triiodophenoxymethylcyclopentane and 2-(2,4,6-triiodophenoxy)ethylcyclopentane.

6. The composition according to claim 1 wherein said x-ray contrast agent is selected from the group consisting of: (E,E)-1-(2,4,6-triiodophenoxy)-3,7,11-trimethyl-2,6,10-dodecatriene, 1-(2,4,6-triiodophenoxy)-3,7-dimethyl-6-octene, (E)-1-(3,5-dimethyl-2,4,6-triiodophenoxy)-3,7-dimethyl-2,6-octadiene and (E)-1-(2,4,6-triiodophenoxy)-3,7-dimethyl-2,6-octadiene.

7. The composition according to claim 1 wherein said x-ray contrast agent is selected from the group consisting of: 1-(2,4,6-triiodophenoxy)-3-octyne, 2-(2,4,6-triiodophenoxy)-4-octyne, 1-(2,4,6-triiodophenoxy)-3-octyne, diethyl 2-(2,4,6-triiodophenoxy)-1,3-propanedioate and diisopropyl 2-(2,4,6-triiodophenoxy)-1,3-propanedioate.

8. The composition according to claim 1 wherein said x-ray contrast agent is selected from the group consisting of: ethyl 2,2-bis-(3-iodophenoxy)acetate, ethyl-5-(2,4,6-triiodophenoxy)-hexanoate, 5-(2,4,6-triiodophenoxy)-hexan-1-ol, 10-(4-iodophenoxy)-undecan-1-ol, ethyl 5-(2,4,6-triiodophenoxy)-hexyl carbonate and ethyl 10-(3-iodophenoxy)-undecanoate.

9. The x-ray contrast composition of claim 1 wherein said polymeric material is anionic having the formula:

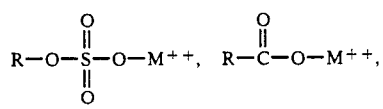

wherein
R is the polymeric chain;

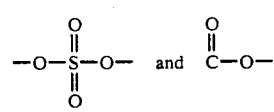

are anionic ligands; and
$M^{++}$ is a divalent cation.

10. The x-ray contrast composition of claim 9 wherein said anionic polymeric material is a sulfated polysaccharide having the formula:

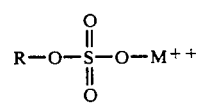

wherein
R is
3,6-anhydro-D-galactose linked through C-4 to D-galactose; (kappa carrageenan)
α-D-galactose units (1-3) linked; (lambda carrageenan)
D-galactose 3,6-anhydro-D-galactose; (iota carrageenan)
D-galactose 3,6-anhydro-L-galactose: (Agar-Agar)
D-galactose
3,6-anhydro-D-galactose; (Furcellaren)
D-glucopyranose; (Laminarin sulfate)
Galactan; and (Galactan sulfate)
Galactosamino-glucuronans (Chondroitin sulfates); and
$M^{++}$ is $Mg^{++}$, $Ca^{++}$, $Zn^{++}$, $Ba^{++}$ or a mixture thereof.

11. The x-ray contrast composition of claim 9 wherein said anionic polymeric material is a carboxylated polysaccharide having the formula:

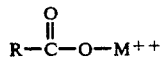

wherein
R is
D-galacturonoglycan; and (Pectin)
anhydro-D-mannuronic acid and anhydro-L-guluronic acid (Algin) residues; and
$M^{++}$ is $Mg^{++}$, $Ca^{++}$, $Zn^{++}$, $Ba^{++}$ or a mixture thereof.

12. The x-ray contrast composition of claim 9 wherein said anionic polymeric material is a cellulose derivative of the formula:

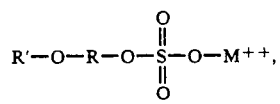

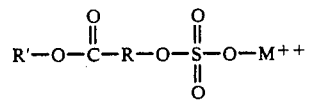

and

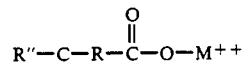

wherein
R is an anhydroglucose residue;
R' is $CH_3$, $C_2H_5$ or $C_3H_7$;
R" is $CH_3$ or $C_2H_5$; and
$M^{++}$ is $Mg^{++}$, $Ca^{++}$, $Zn^{++}$, $Ba^{++}$ or a mixture thereof.

13. The x-ray contrast composition of claim 12 wherein said cellulose derivative is selected from the group consisting of sodium ethylcellulose sulfate, sodium cellulose acetate sulfate and sodium carboxymethyl cellulose.

14. The x-ray contrast composition of claim 1 wherein said anionic polymeric material is a sulfated, sulfonated or carboxylated synthetic polymer having the formula:

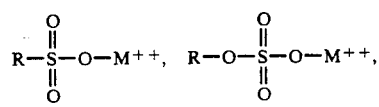

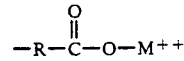

wherein
R is an aliphatic or aromatic hydrocarbon; and
$M^{++}$ is $Mg^{++}$, $Ca^{++}$, $Zn^{++}$, $Ba^{++}$ or a mixture thereof.

15. The x-ray contrast composition of claim 1 wherein said polymeric material is cationic selected from the group consisting of: dermatan sulfate, keratosulfate, hyaluronic acid, heparin and chitin.

16. The x-ray contrast composition of claim 1 wherein said polymeric material is a polysaccharide.

17. The x-ray contrast composition of claim 16 wherein said polysaccharide is selected from the group consisting of starch, glycogen, glucan, fructans, mannans, galactomannans, flucomannas, galactans, xylans, glycuranans, dextran and starch amylose.

18. The x-ray contrast composition of claim 1 wherein said polymeric material is a cellulose derivative.

19. The x-ray contrast composition of claim 18 wherein said cellulose derivative is selected from the group consisting of methylcellulose, hydroxyethyl cellulose, ethylhydroxyethyl and hydroxypropyl cellulose.

20. The x-ray contrast composition of claim 1 wherein said polymeric material is polyvinylpyrrolidone, polyvinyl alcohol or an ethylene oxide polymer.

21. The x-ray contrast composition of claim 1 wherein said pharmaceutical carrier contains at least one surfactant.

22. The x-ray contrast composition of claim 21 wherein said surfactant is cationic.

23. The x-ray contrast composition of claim 21 wherein said surfactant is anionic.

24. The x-ray contrast composition of claim 21 wherein said surfactant is zwitterionic.

25. The x-ray contrast composition of claim 21 wherein said surfactant is nonionic.

26. The x-ray contrast composition of claim 22 wherein said cationic surfactant is selected from the group consisting of cetyl trimethyl ammonium bromide and dodecyl dimethyl ammonium bromide.

27. The x-ray contrast composition of claim 23 wherein said anionic surfactant is selected form the group consisting of sodium lauryl sulfate, sodium heptadecyl sulphate, an alkyl benzene sulphonic acid, sodium butylnaphthalene sulfonate and sulphosuccinate.

28. The x-ray contrast composition of claim 25 wherein said nonionic surfactant is selected from the group consisting of carboxylic esters, carboxylic amides, ethoxylated alkylphenols and ethoxylated aliphatic alcohols, sorbitan esters, polyoxyethylene alkyl ethers and polyoxyethylene sorbitan fatty acid esters.

29. A method of carrying out x-ray examination of the gastrointestinal tract of a patient, said method comprises the oral or rectal administration to the patient an x-ray contrast composition according to claim 1.

* * * * *